(12) United States Patent
Haack et al.

(10) Patent No.: US 10,551,383 B2
(45) Date of Patent: Feb. 4, 2020

(54) METHODS OF DETECTING A POLYPEPTIDE HAVING ANAPLASTIC LYMPHOMA KINASE ACTIVITY IN KIDNEY CANCER

(71) Applicant: Cell Signaling Technology, Inc., Danvers, MA (US)

(72) Inventors: Herbert Haack, South Hamilton, MA (US); Katherine Eleanor Crosby, Middleton, MA (US); Victoria McGuinness Rimkunas, Reading, MA (US); Matthew Ren Silver, Rockport, MA (US)

(73) Assignee: CELL SIGNALING TECHNOLOGY, INC., Danvers, MA (US)

( * ) Notice: Subject to any disclaimer, the term of this patent is extended or adjusted under 35 U.S.C. 154(b) by 0 days.

(21) Appl. No.: 14/844,832

(22) Filed: Sep. 3, 2015

(65) Prior Publication Data

US 2015/0369810 A1    Dec. 24, 2015

Related U.S. Application Data

(63) Continuation of application No. 13/204,342, filed on Aug. 5, 2011, now abandoned.

(60) Provisional application No. 61/371,525, filed on Aug. 6, 2010.

(51) Int. Cl.
| | |
|---|---|
| *G01N 33/574* | (2006.01) |
| *A61K 31/4162* | (2006.01) |
| *A61K 31/4545* | (2006.01) |
| *A61K 31/517* | (2006.01) |
| *C12Q 1/6886* | (2018.01) |

(52) U.S. Cl.
CPC ... *G01N 33/57484* (2013.01); *A61K 31/4162* (2013.01); *A61K 31/4545* (2013.01); *A61K 31/517* (2013.01); *C12Q 1/6886* (2013.01); *G01N 33/57438* (2013.01); *C12Q 2600/112* (2013.01)

(58) Field of Classification Search
CPC ............ A61K 31/4162; A61K 31/4545; A61K 31/517; G01N 2333/70596; G01N 2800/52; G01N 33/57438; G01N 33/57484; C12Q 1/6886; C12Q 2600/112
See application file for complete search history.

(56) References Cited

U.S. PATENT DOCUMENTS

| | | |
|---|---|---|
| 5,529,925 A | 6/1996 | Morris et al. |
| 7,605,131 B2 | 10/2009 | Mano et al. |
| 7,728,120 B2 | 6/2010 | Mano et al. |
| 2003/0099974 A1 | 5/2003 | Lillie et al. |
| 2008/0090776 A1 | 4/2008 | Mano et al. |
| 2009/0099193 A1 | 4/2009 | Mano et al. |
| 2012/0101108 A1 | 4/2012 | Haack et al. |

FOREIGN PATENT DOCUMENTS

| | | |
|---|---|---|
| EP | 1 454 992 A1 | 9/2004 |
| EP | 1 914 240 A1 | 4/2008 |
| EP | 2 116 553 A1 | 11/2009 |
| JP | 2008-295444 A | 12/2008 |
| WO | 2005/054237 A1 | 6/2005 |
| WO | 2005/056752 A2 | 6/2005 |
| WO | 2005/083439 A1 | 9/2005 |
| WO | 2009/102446 A2 | 8/2009 |
| WO | 2010/069966 A1 | 6/2010 |
| WO | 2010/132888 A2 | 11/2010 |
| WO | 2011/095894 A2 | 8/2011 |
| WO | 2011/146945 A2 | 11/2011 |

OTHER PUBLICATIONS

Boyle, M.B., "Voltage-Dependent Sodium Channel Alpha Subunit" Medline [online], Medline Accession No. Q80WH9 http://www.ncbi.nlm.nih.gov/protein/q80wh9 (Oct. 31, 2006).
Bridge, J. et al., "Fusion of the ALK Gene to the Clathrin Heavy Chain Gene, CLTC, in Inflammatory Myofibroblastic Tumor", American Journal of Pathology 159(2):411-415 (Aug. 2001).
Chiarle R. et al., "The Anaplastic Lymphoma Kinase in the Pathogenesis of Cancer", Nature Reviews 8:11-23 (Jan. 2008).
Choi, Y. et al., "Identification of Novel Isoforms of the EML4-ALK Transforming Gene in Non-Small Cell Lung Cancer", Cancer Research 68(13):4971-4976 (Jul. 1, 2008).
Dang, T.P. et al., "Chromosome 19 Translocation, Over expression of Notch3, and Human Lung Cancer", Journal of the National Cancer Institute 92(16):1355-1357 (Aug. 16, 2000).
Debelenko L.V. et al., "Renal Cell Carcinoma With Novel VCL-ALK Fusion: New Representative of ALK-Associated Tumor Spectrum", Modern Pathology 24:430-442 (2011).
Drabkin, H.A. et al., "DEF-3(916/NT-LU-12), an RNA Binding Protein From the 3p21.3 Homozygous Deletion Region in SCLC", Oncogene 18(16):2589-2597 (1999).
Falini, B. et al., "Proteins Encoded by Genes Involved in Chromosomal Alterations in Lymphoma and Leukemia: Clinical Value of Their Detection by Immunocytochemistry" Blood 99(2):409-429 (Jan. 15, 2002).
Falini, B. et al., "ALK Expression Defines a Distinct Group of T/Null Lymphomas ("ALK Lymphomas") with a Wide Morphological Spectrum", American Journal of Pathology 153(3):875-886 (Sep. 3, 1998).
Gerber, S.A. et al., "Absolute Quantification of Proteins and Phosphoproteins from Cell Lysates by Tandem MS", Proceedings of the National Academy of Sciences (USA) 100(12):6940-6945 (Jun. 10, 2003).

(Continued)

*Primary Examiner* — Delia M Ramirez
(74) *Attorney, Agent, or Firm* — Scully, Scott, Murphy & Presser, P.C.

(57) ABSTRACT

The invention provides methods to identify, diagnose, and treat kidney cancer through the detection of expression and/or activity of anaplastic lymphoma kinase (ALK). The detection of the presence of a polypeptide with ALK kinase activity (e.g., by detecting expression and/or activity of the polypeptide), identify those kidney cancers that are likely to respond to an ALK-inhibiting therapeutic.

5 Claims, 4 Drawing Sheets

Specification includes a Sequence Listing.

(56) References Cited

OTHER PUBLICATIONS

Hernandez, L. et al., "TRK-Fused Gene (TFG) is a New Partner of ALK in Anaplastic Large Cell Lymphoma Producing Two Structurally Different TFG-ALK Translocations", Blood 94(9):3265-3268 (Nov. 1, 1999).
Hernandez, L. et al., "Diversity of Genomic Breakpoints in TFG-ALK Translocations in Anaplastic Large Cell Lymphomas: Identification of a New TFG-ALKxL Chimeric Gene with Transforming Activity", American Journal of Pathology 160(4):1487-1494 (Apr. 2002).
Horn, L. et al., "EML4-ALK: Honing in on a New Target in Non-Small-Cell Lung Cancer", Journal of Clinical Oncology 27(26):4232-4235 (Sep. 10, 2009).
Inman G.J. et al., "SB-431542 is a Potent and Specific Inhibitor of Transforming Growth Factor-B Superfamily Type I Activin Receptor-Like Kinase (ALK) Receptors ALK4, ALK5, and ALK7", Molecular Pharmacology 62(1):65-74 (2002).
Iwahara, T. et al., "Molecular Characterization of ALK, a Receptor Tyrosine Kinase Expressed Specifically in the Nervous System", Oncogene 14:439-449 (1997).
Kovacs G. et al., "Specific Chromosome Aberration in Human Renal Cell Carcinoma", Int. J. Cancer 40:171-178 (1987).
Kurzrock, R. et al., "The Molecular Genetics of Philadelphia Chromosome-Positive Leukemias", The New England Journal of Medicine 319(15):990-998 (Oct. 13, 1988).
Lamant, L. et al., "A New Fusion Gene TPM3-ALK in Anaplastic Large Cell Lymphoma Created by a (1;2) (q25;p23) Translocation", Blood 93(9):3088-3098 (May 1, 1999).
Marzec et al., "Inhibition of ALK Enzymatic Activity in T-Cell Lymphoma Cells Induces Apoptosis and Suppresses Proliferation and STAT3 Phosphorylation Independently of Jak3", Laboratory Investigation 85:1544-1554 (2005).
Morris, S. et al., "ALK, the Chromosome 2 Gene Locus Altered by the t(2;5) in Non-Hodgkin's Lymphoma, Encodes a Novel Neural Receptor Tyrosine Kinase that is Highly Related to Leukocyte Tyrosine Kinase (LTK)", Oncogene 14 (18):2175-2188 (1997).
Morris, S.W. et al., "Fusion of a Kinase Gene, ALK, to a Nucleolar Protein Gene, NPM, in Non-Hodgkin's Lymphoma", Science 263:1281-1284 (Mar. 4, 1994).
Osajima-Hakomori, Y. et al., "Biological Role of Anaplastic Lymphoma Kinase in Neuroblastoma", American Journal of Pathology 167(1):213-222 (Jul. 2005).
Oyama et al., "Molecular Genetic Tumor Markers in Non-small Cell Lung Cancer", Anticancer Research 25:1193-1196 (2005).
Pavlovich C.P. et al., "Patterns of Aneuploidy in Stage IV Clear Cell Renal Cell Carcinoma Revealed by Comparative Genomic Hybridization and Spectral Karyotyping", Genes, Chromosomes & Cancer 37:252-260 (2003).
Perner S. et al., "EML4-ALK Fusion Lung Cancer: A Rare Acquired Event", Neoplasia 10(3):298-302 (Mar. 2008).
Pulford K. et al., "Detection of Anaplastic Lymphoma Kinase (ALK) and Nucleolar Protein Nucleophosmin (NPM)-ALK Proteins in Normal and Neoplastic Cells With the Monoclonal Antibody ALK1", Blood 89(4):1394-1404 (Feb. 15, 1997).
Pulford et al., "Anaplastic Lymphoma Kinase Proteins in Growth Control and Cancer", Journal of Cellular Physiology 199(3):330-358 (2004).
Shiota, M. et al., "Diagnosis of t(2;5) (p23;q35)-Associated Ki-1 Lymphoma With Immunohistochemistry", Blood 84 (11):3648-3652 (Dec. 1, 1994).
Soda et al., "Identification of the Transforming EML4-ALK Fusion Gene in Non-small Lung Cancer", Nature 448:561-566 (2007).
Takeuchi K. et al., "KIF5B-ALK, A Novel Fusion Oncokinase Identified by an Immunohistochemistry-Based Diagnostic System for ALK-Positive Lung Cancer", Clin Cancer Res 15(9):3143-3149 (May 1, 2009).
Tort, F. et al., "Molecular Characterization of a New ALK Translocation Involving Moesin (MSN-ALK) in Anaplastic Large Cell Lymphoma", Laboratory Investigation 81(3):419-426 (Mar. 2001).
Touriol, C. et al., "Further Demonstration of the Diversity of Chromosomal Changes Involving 2p23 in ALK-Positive Lymphoma: 2 Cases Expressing ALK Kinase Fused to CLTCL (Clathrin Chain Polypeptide-Like)", Blood 95 (10):3204-3207 (May 15, 2000).
Yoshida M.A. et al., "Cytogenetic Studies of Tumor Tissue from Patients with Nonfamilial Renal Cell Carcinoma", Cancer Research 46:2139-2149 (Apr. 1986).
Zhao W.P. et al., "Renal Cell Carcinoma", Cancer Genet Cytogenet 82:128-139 (1995).
Database Uniport "SubName: Full=Voltage-dependent Sodium Channel Alpha Subunit; Flags: Fragments" (Jun. 1, 2003) [OnLine].
Database Geneseq "Rice Abiotic Stress Responsive Polypeptide SEQ ID No. 7811" (Jun. 2, 2005) [OnLine].
Genebank database, Jun. 27, 1996, Accession No. U55187.1.
UniProt Database, Jun. 1, 2003, EBI Accession No. Q80WH9_9MURI.
Japanese Notice of Reason for Refusal dated Nov. 15, 2011 received from Application No. 2009-525538, together with an English-language translation.
International Search Report dated Aug. 29, 2008 issued in corresponding International Application No. PCT/US2007/09273.
Canadian Office Action dated Mar. 24, 2011 received from Application No. 2,648,864.
International Search Report and Written Opinion dated Jan. 30, 2012 received from Application No. PCT/US2011/046807.

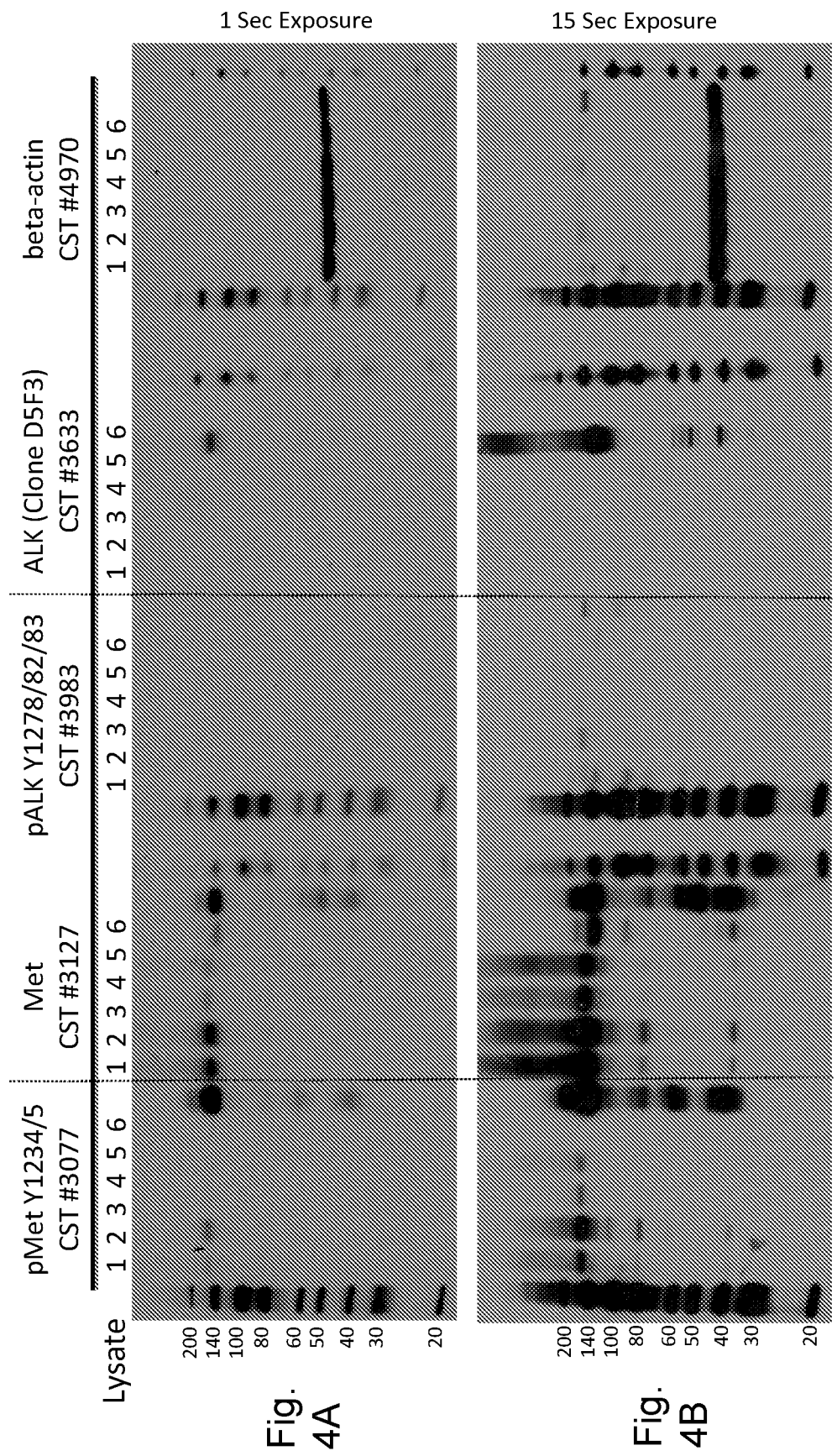

METHODS OF DETECTING A POLYPEPTIDE HAVING ANAPLASTIC LYMPHOMA KINASE ACTIVITY IN KIDNEY CANCER

CROSS REFERENCE TO RELATED APPLICATIONS

The application is a continuation of U.S. patent application Ser. No. 13/204,342, filed Aug. 5, 2011, which claims priority to U.S. Provisional Application Ser. No. 61/371,525 filed Aug. 6, 2010, the entire contents of which are hereby incorporated by reference.

FIELD OF THE INVENTION

The invention relates generally to proteins and genes involved in cancer (e.g., kidney cancer), and to the detection, diagnosis and treatment of cancer.

BACKGROUND OF THE INVENTION

Many cancers are characterized by disruptions in cellular signaling pathways that lead to aberrant control of cellular processes, or to uncontrolled growth and proliferation of cells. These disruptions are often caused by changes in the activity of particular signaling proteins, such as kinases.

Aberrant expression of protein kinase proteins can be the causative agent of (and the driver of) cancer. Aberrant expression can be caused by the fusion of the protein (or kinase portion thereof) with a secondary protein (or portion there), expression of a truncated portion of the protein, or by abnormal regulation of expression of the full-length protein.

It is known that gene translocations resulting in kinase fusion proteins with aberrant signaling activity can directly lead to certain cancers (see, e.g., Mitelman et al., Nature Reviews Cancer 7: 233-245, 2007, Futreal et al., Nat Rev Cancer 4(3): 177-183 (2004), and Falini et al., *Blood* 99(2): 409-426 (2002). For example, it has been shown that the BCR-ABL oncoprotein, a tyrosine kinase fusion protein, is the causative agent and drives human chronic myeloid leukemia (CML). The BCR-ABL oncoprotein, which is found in at least 90-95% of CML cases, is generated by the translocation of gene sequences from the c-ABL protein tyrosine kinase on chromosome 9 into BCR sequences on chromosome 22, producing the so-called Philadelphia chromosome. See, e.g. Kurzock et al., *N. Engl. J. Med.* 319: 990-998 (1988). The translocation is also observed in acute lymphocytic leukemia (ALL) and acute myeloid leukemia (AML) cases. These discoveries spurred FDA approval of imatinib mesylate (sold under the trademark Gleevec® by Novartis) and dasatinig (sold by Bristol-Mysers Squibb under the trademark Sprycel®), small molecule inhibitors of the ABL kinase, for the treatment of CML and ALL. These drugs are examples of drugs that are designed to interfere with the signaling pathways that drive the growth of tumor cells. The development of such drugs represents a significant advance over the conventional therapies for CML and ALL, chemotherapy and radiation, which are plagued by well known side-effects and are often of limited effect since they fail to specifically target the underlying causes of the malignancies.

Thus, it would be useful to identify proteins that drive cancers in order to detect cancers at an early stage, when they are more likely to respond to therapy, and for the development of new reagents and methods for the study, diagnosis, and treatment of such cancers. Additionally, identification of such proteins will, among other things, desirably enable new methods for selecting patients for targeted therapies, as well as for the screening and development of new drugs that inhibit such proteins and, thus, treat cancer.

SUMMARY OF THE INVENTION

The invention is based on the discovery of ALK kinase in kidney cancer cells. This unexpected discovery enables methods to detect, treat, and cure kidney cancers driven by ALK kinase activity.

In a first aspect, the invention provides a method for detecting the presence and/or activity of a polypeptide with ALK kinase activity in a biological sample from a mammalian kidney cancer or suspected mammalian kidney cancer. The method includes (a) obtaining a biological sample from a mammalian kidney cancer or suspected mammalian kidney cancer and (b) contacting the biological sample with a detection molecule selected from the group consisting of a reagent that detects ALK kinase activity, a reagent that detects a polypeptide with ALK kinase activity, and a reagent that detects to a polynucleotide encoding the polypeptide with ALK kinase activity, and (c) detecting reaction of the detection molecule with the biological sample, wherein reaction of the detection molecule with the biological sample indicates said polypeptide with ALK kinase activity is present or active in said mammalian kidney cancer or suspected mammalian kidney cancer. In some embodiments, the detection molecule is detectably labeled.

In another aspect, the invention provides a method for identifying a mammalian kidney cancer or suspected mammalian kidney cancer that belongs to a subset of kidney cancers driven by ALK kinase activity, said method comprising the steps of (a) contacting a biological sample obtained from a mammalian kidney cancer or suspected mammalian kidney cancer with at least one detection molecule selected from the group consisting of a reagent that detects ALK kinase activity, a reagent that detects a polypeptide with ALK kinase activity, and a reagent that detects to a polynucleotide encoding the polypeptide with ALK kinase activity, and (b) detecting reaction of the detection molecule with said biological sample, wherein the reaction of the detection molecule with said biological sample indicates that said mammalian kidney cancer or suspected mammalian kidney cancer is driven by ALK kinase activity. In some embodiments, the mammalian kidney cancer or suspected mammalian kidney cancer driven by ALK kinase activity is likely to respond to a composition comprising at least one ALK-inhibiting therapeutic.

In another aspect, the invention provides method for determining whether a compound inhibits the progression of a mammalian kidney cancer or suspected mammalian kidney cancer driven by a polypeptide with ALK kinase activity, said method comprising the step of determining whether said compound inhibits the expression and/or activity of said polypeptide in said cancer mammalian kidney cancer or suspected mammalian kidney cancer.

In another aspect, the invention provides a method for inhibiting the progression of a mammalian kidney cancer or suspected mammalian kidney cancer driven by polypeptide with ALK kinase activity, comprising inhibiting the expression and/or activity of said polypeptide in said mammalian kidney cancer or suspected mammalian kidney cancer.

In another aspect, the invention provides a method for treating a mammalian patient with mammalian kidney cancer or suspected mammalian kidney cancer driven by a polypeptide with ALK kinase activity, said method comprising the step of administering a composition comprising a therapeutically effective amount of a composition comprising an ALK-inhibiting therapeutic to the mammalian patient.

In still a further aspect, the invention provides a method for treating a patient having a mammalian kidney cancer or suspected mammalian kidney cancer comprising the steps of: (a) detecting the presence or activity of said polypeptide with ALK kinase activity a biological sample of the mammalian kidney cancer or suspected mammalian kidney cancer of the patient; and (b) administering a composition comprising an ALK-inhibiting therapeutic to the patient. In some embodiments, the patient is a human.

In various embodiments of all of the aspects of the invention, the method for detecting the presence and/or activity of a polypeptide with ALK kinase activity in a biological sample from a mammalian kidney cancer or suspected mammalian kidney cancer comprising the steps of: (a) obtaining a biological sample from a mammalian kidney cancer or suspected mammalian kidney cancer and (b) contacting the biological sample with a reagent that detects ALK kinase activity, wherein detection of ALK kinase activity by the reagent in the biological sample indicates said polypeptide with ALK kinase activity is present in said biological sample. In some embodiments, the method for detecting the presence and/or activity of a polypeptide with ALK kinase activity in a biological sample from a mammalian kidney cancer or suspected mammalian kidney cancer comprises the steps of: (a) obtaining a biological sample from a mammalian kidney cancer or suspected mammalian kidney cancer and (b) contacting the biological sample with a reagent that detects a polypeptide with ALK kinase activity, wherein detection of said polypeptide in said biological sample indicates said polypeptide with ALK kinase activity is present in said biological sample. In some embodiments, the method for detecting the presence and/or activity of a polypeptide with ALK kinase activity in a biological sample from a mammalian kidney cancer or suspected mammalian kidney cancer comprises the steps of: (a) obtaining a biological sample from a mammalian kidney cancer or suspected mammalian kidney cancer and (b) contacting the biological sample with a reagent that detects a polynucleotide encoding the polypeptide with ALK kinase activity, wherein detection of said polynucleotide in said biological sample indicates said polypeptide with ALK kinase activity is present in said biological sample.

In various embodiments of all of the aspects of the invention, the inhibition of the expression and/or activity of the polypeptide is determined using a reagent that detects ALK kinase activity, a reagent that detects a polypeptide with ALK kinase activity, or a reagent that detects to a polynucleotide encoding the polypeptide with ALK kinase activity.

In various embodiments of all of the aspects of the invention, the detection molecule is detectably labeled.

In various embodiments of all of the aspects of the invention, the mammalian kidney cancer or suspected mammalian kidney cancer in which the presence or activity of said polypeptide with ALK kinase activity is detected is identified as a mammalian kidney cancer or suspected mammalian kidney cancer belonging to a subset of kidney cancers driven by ALK kinase activity. In some embodiments, the mammalian kidney cancer or suspected mammalian kidney cancer in which the presence or activity of said polypeptide with ALK kinase activity is detected is identified as a mammalian kidney cancer or suspected mammalian kidney cancer likely to respond to an ALK-inhibiting therapeutic.

In various embodiments of all of the aspects of the invention, the polypeptide with ALK kinase activity is aberrantly expressed full-length ALK protein. In various embodiments, the polypeptide with ALK kinase activity is an ALK fusion polypeptide comprising at least a portion of a first fusion member and at least a portion of a second fusion member, wherein the second fusion member is an ALK protein comprises an ALK kinase domain. In some embodiments, the portion of the ALK protein In some embodiments, the first fusion member is an NPM polypeptide, a ALO17 polypeptide, a TFG polypeptide, a MSN polypeptide, a TPM3 polypeptide, a TPM4 polypeptide, an ATIC polypeptide, a MYH9 polypeptide, a CLTC polypeptide, a SEC31L1 polypeptide, an RANBP2 polypeptide, a CARS polypeptide, an EML4 polypeptide, a KIF5B polypeptide, or a VCL polypeptide. In some embodiments, the ALK fusion polypeptide is an NPM-ALK fusion polypeptide, an ALO17-ALK fusion polypeptide, an MSN-ALK fusion polypeptide, an TPM3-ALK fusion polypeptide, an TPM4-ALK fusion polypeptide, an ATIC-ALK fusion polypeptide, an MYH9-ALK fusion polypeptide, an CLTC-ALK fusion polypeptide, an SEC31L1-ALK fusion polypeptide, an RANBP2-ALK fusion polypeptide, an CARS-ALK fusion polypeptide, an EML4-ALK fusion polypeptide, an KIF5B-ALK fusion polypeptide, a TFG-ALK fusion polypeptide, or a VCL-ALK fusion polypeptide.

In various embodiments of all of the aspects of the invention, the polypeptide with ALK kinase activity is a truncated ALK polypeptide. In some embodiments, the reagent that detects ALK kinase activity is a substrate of ALK. In some embodiments, the method is implemented in an in vitro kinase assay format. In some embodiments, the method is implemented in an immunological assay employing a phosphorylated tyrosine-specific binding agent (e.g., an antibody that specifically binds to phosphorylated tyrosine residues).

In various embodiments of all of the aspects of the invention, the reagent that detects a polypeptide with ALK kinase activity is a reagent that specifically binds to the polypeptide. In some embodiments, the reagent that specifically binds to the polypeptide is an antibody. In some embodiments, the reagent that specifically binds to the polypeptide is an AQUA peptide. In some embodiments, the antibody specifically binds to a full length ALK protein.

In various embodiments of all of the aspects of the invention, where the protein with ALK kinase activity is a ALK fusion polypeptide, the reagent that detects a polypeptide with ALK kinase activity is reagent that specifically binds the ALK fusion polypeptide. In some embodiments, the reagent that specifically binds to the ALK fusion polypeptide is an antibody. In some embodiments, the reagent that specifically binds to the ALK fusion polypeptide is an AQUA peptide. In some embodiments, the antibody specifically binds to the portion of the ALK protein present in the ALK fusion, to the portion of the first fusion member present in the ALK fusion, or to a junction between the first fusion member and the portion of the ALK protein present in the ALK fusion.

In various embodiments of all of the aspects of the invention, the method is implemented in a flow cytometry assay format, an immunohistochemistry (IHC) assay format, an immunofluorescence (IF) assay format, an Enzyme-linked immunosorbent assay (ELISA) assay format, a Western blotting analysis assay format, or a mass spectrometry assay format.

In various embodiments of all of the aspects of the invention, the reagent that detects a polynucleotide encoding the polypeptide with ALK kinase activity is a nucleic acid molecule that hybridizes to said polynucleotide. In some embodiments, the nucleic acid molecule hybridizes to the polynucleotide under stringent conditions.

In various embodiments of all of the aspects of the invention, the nucleic acid molecule is a polymerase chain reaction (PCR) probe, a fluorescence in situ hybridization (FISH) probe, or a Southern blotting probe. In some embodiments, the method is implemented in a polymerase chain reaction (PCR) assay format, a in situ hybridization (ISH) assay format, or a Southern blotting assay format.

In various embodiments of all of the aspects of the invention, the mammalian kidney cancer or suspected mammalian kidney cancer is a granular cell cancer or a squamous cell cancer. In various embodiments, the mammalian kidney cancer or suspected mammalian kidney cancer is from a mammal. In various embodiments, the mammalian kidney cancer or suspected mammalian kidney cancer is from a human.

In various embodiments of all of the aspects of the invention, the biological sample is a circulating tumor cell from said mammalian kidney cancer or suspected mammalian kidney cancer. In certain embodiments, the biological sample is a tissue biopsy or a fine needle aspirate from said mammalian kidney cancer or suspected mammalian kidney cancer.

In various embodiments of all of the aspects of the invention, a patient from whom said biological sample is obtained is diagnosed as having a mammalian kidney cancer or suspected mammalian kidney cancer driven by the polypeptide with ALK kinase activity. In some embodiments, the patient is administered pharmaceutical composition comprising an ALK-inhibiting therapeutic (e.g., PF-02341066, NVT TAE-684, AP26113, CEP-14083, CEP-14513, CEP11988, WHI-P131 or WHI-P154).

In various embodiments of all of the aspects of the invention, the expression and/or activity of the polypeptide with ALK kinase activity is inhibited with a composition comprising an ALK-inhibiting therapeutic. In some embodiments, the ALK-inhibiting therapeutic is PF-02341066 (also known as crizotinib). In some embodiments, the ALK-inhibiting therapeutic is NVT TAE-684, AP26113, or CEP-14083, CEP-14513, CEP11988, WHI-P131 and WHI-P154.

In still another aspect, the invention provides methods for diagnosing kidney cancer in a patient (also referred to as a subject). The methods comprise obtaining a biological sample from a subject suspected of having kidney cancer, obtaining a control biological sample from a normal individual not suspected of having kidney cancer, measuring the level of expression and/or activity of a polypeptide with ALK kinase activity or polynucleotide encoding a polypeptide with ALK kinase activity in the biological sample and control biological sample using a detection device, generating a database of the detected levels of expression and/or activity of said polypeptide with ALK kinase activity or polynucleotide in the biological sample and control biological sample, and obtaining a report from the database of the detection device wherein a higher level of expression and/or activity of the polypeptide with ALK kinase activity or polynucleotide in the biological sample relative to the control biological sample is correlated to a kidney cancer diagnosis. Suitably, the kidney cancer is likely to respond to treatment with an ALK inhibitor (i.e., an ALK-inhibiting therapeutic).

In certain embodiments, the polynucleotide encoding a polypeptide with ALK kinase activity is an mRNA or cDNA encoding full-length ALK protein or encoding an ALK fusion polypeptide, including a ALK fusion polypeptide comprising the intracellular domain of ALK, the tyrosine kinase domain of ALK, or the C-terminal domain of ALK. Detecting of the mRNA can be performed by any method including, for example, by RT-PCR or Northern blot analysis.

The polypeptide with ALK kinase activity can be detected by an antibody specific for the intracellular domain of ALK, including an antibody that does not cross-react with c-Met, and an antibody that is specific for the tyrosine kinase domain of ALK.

In another embodiment, the polypeptide with ALK kinase activity can be detected using a reagent that is specific for an ALK fusion polypeptide comprising amino acids 1376-1620 of full length ALK (where full length ALK is 1620 amino acids and is set forth in SEQ ID NO: 2), amino acid residues 1504-1507 of full length ALK, or amino acid residues 1603-1606 of full length ALK.

In embodiments, the ALK fusion polypeptide is selected from the group consisting of VCL-ALK, EML4-ALK, NPM-ALK, TPM3-ALK, TFG-ALK, ATIC-ALK, CLTC-ALK, MSN-ALK, TPM4-ALK, ALO17-ALK, RANBP2-ALK, MYH9-ALK, CARS-ALK, SEC31L1-ALK, and KIF5B-ALK.

In additional aspects, the invention provides methods for treating a kidney cancer in a patient (also referred to as a subject). The methods comprise obtaining a biological sample from a patient suspected of having kidney cancer, obtaining a control biological sample from a normal individual not suspected of having kidney cancer, detecting a level of expression and/or activity of a polypeptide with ALK kinase activity in the biological sample and the control biological sample and treating the subject with an ALK inhibitor if the level of expression and/or activity of the polypeptide with ALK kinase activity in the biological sample is greater than the level of expression and/or activity of the polypeptide with ALK kinase activity in the control biological sample.

In further aspects, the invention provides methods for diagnosing kidney cancer in a subject comprising obtaining a biological sample from a patient suspected of having kidney cancer and determining whether a polypeptide with ALK kinase activity or polynucleotide encoding the same is present in the biological sample.

The invention also provides methods for treating a kidney cancer in a patient comprising obtaining a biological sample from a patient suspected of having kidney cancer, determining whether a polypeptide with ALK kinase activity or polynucleotide encoding the same is present in the biological sample and treating the patient with an ALK inhibitor if the polypeptide with ALK kinase activity or polynucleotide encoding the same is present.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 4A depicts a Western blot of MDCK cell lysates probed with antibodies directed to pMet Y1234/5 antibody (Cell Signaling Technology, Inc., Danvers, Mass.; Catalog #3077), Met (25H2) mouse monoclonal antibody (Cell Signaling Technology #3127), pALK Y1278/82/83 antibody (Cell Signaling Technology, #3983), ALK (D5F3) XP®RmAb (Cell Signaling Technology #3633), and Beta Actin (Cell Signaling Technology #4970) after a 1 second exposure. The lanes represented MDCK serum starved overnight (lane 1), MDCK serum starved overnight, followed by HGF stimulation (50 ng/ml) for 5 minutes (lane 2), MDCK serum starved overnight, then serum starved over 24 hours (lane 3), MDCK serum starved followed by HGF stimulation (50 ng/ml) for 24 hours (lane 4), H3122 cells (positive control for ALK (EML4-ALK v1))(lane 5), and MKN45 cells (positive control for pMet)(lane 6) are depicted.

FIG. 4B depicts a Western blot of MDCK cell lysates probed with antibodies directed to pMet Y1234/5 antibody (Cell Signaling Technology, #3077), Met (25H2) mouse monoclonal antibody (Cell Signaling Technology, #3127), pALK Y1278/82/83 antibody (Cell Signaling Technology #3983), ALK (D5F3) XP®RmAb (Cell Signaling Technology #3633), and Beta Actin (Cell Signaling Technology #4970) after a 15 second exposure. The lanes represented MDCK serum starved overnight (lane 1), MDCK serum starved overnight, followed by HGF stimulation (50 ng/ml) for 5 minutes (lane 2), MDCK serum starved overnight, then serum starved over 24 hours (lane 3), MDCK serum starved followed by HGF stimulation (50 ng/ml) for 24 hours (lane 4), H3122 cells (positive control for ALK (EML4-ALK v1))(lane 5), and MKN45 cells (positive control for pMet) (lane 6) are depicted.

DETAILED DESCRIPTION OF THE PREFERRED EMBODIMENTS

Figure 1:
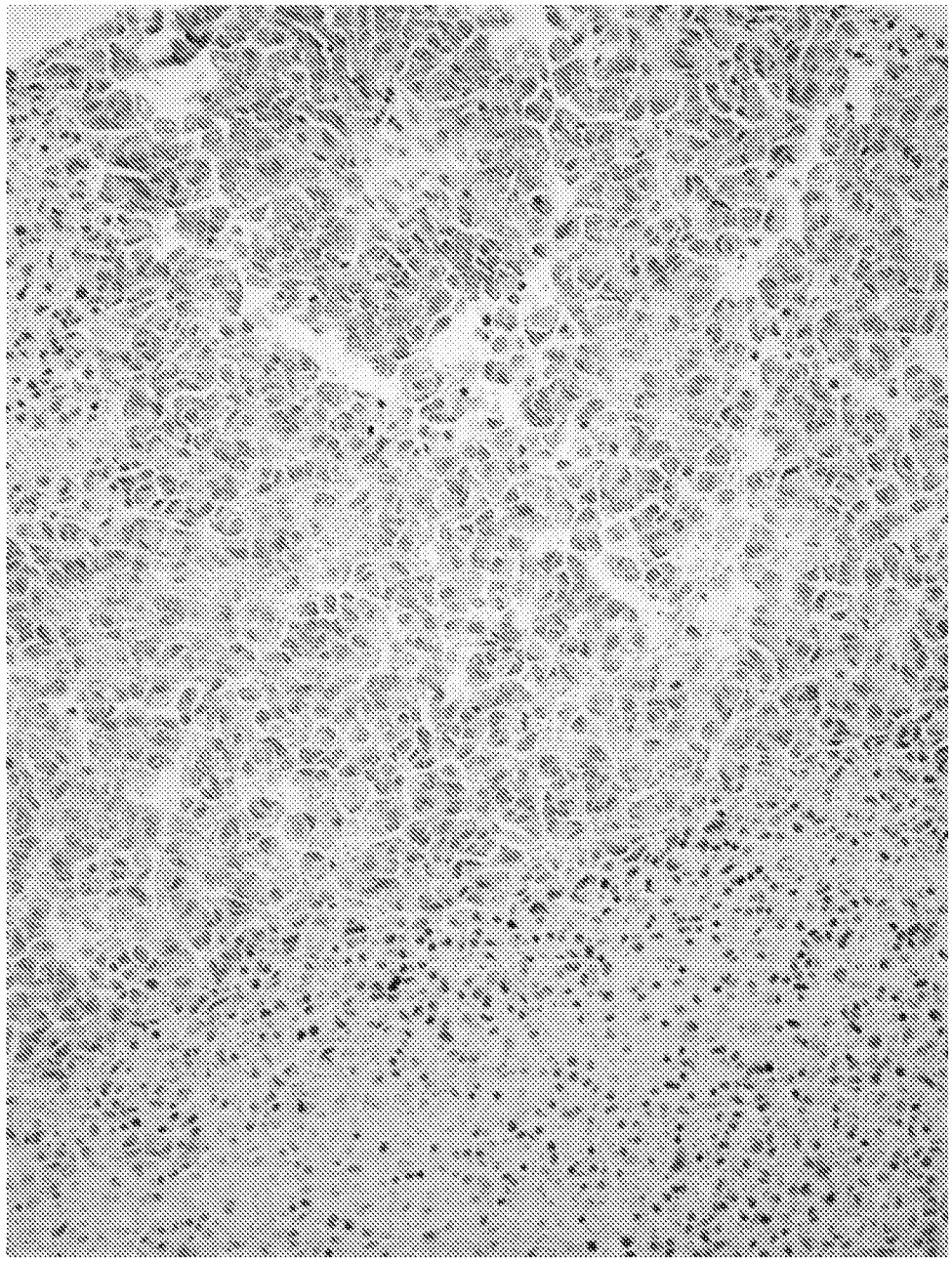
FIG. 1 is an immunohistochemical representation demonstrating ALK-specific monoclonal antibody staining of squamous cell carcinoma of the kidney.

The invention is based upon the unexpected discovery of ALK kinase in human kidney cancer. As ALK kinase is not known to be expressed in normal kidney tissue and cells, the presence of ALK kinase (and ALK kinase activity) is expected to drive the proliferation and survival of the subset of kidney cancer in which it is expressed. Such kidney cancers may be identified (e.g., diagnosed) and/or treated in accordance with the teachings provided herein.

Based on these discoveries, a patient whose kidney cancer (or suspected kidney cancer) expresses a polypeptide with ALK activity where healthy patients (i.e., non-cancerous patients) do not express such proteins with ALK activity in their normal kidney tissue may respond favorably to administration of an ALK inhibitor (e.g., the growth of the kidney cancer may slow or stop as compared to an untreated patient suffering from the same cancer).

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

The further aspects, advantages, and embodiments of the invention are described in more detail below. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Ausubel et al. CURRENT PROTOCOLS IN MOLECULAR BIOLOGY, John Wiley & Sons, New York, N.Y. (1989 and updates through August 2010); Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 11th Ed., McGraw Hill Companies Inc., New York (2006); and Remington: The Science and Practice of Pharmacy, $21^{st}$ Edition, Lippincott Williams & Wilkins, 2005.

In a first aspect, the invention provides a method for detecting the presence and/or activity of a polypeptide with ALK kinase activity in a biological sample from a mammalian kidney cancer or suspected mammalian kidney cancer. The method includes (a) obtaining a biological sample from a mammalian kidney cancer or suspected mammalian kidney cancer and (b) contacting the biological sample with a detection molecule selected from the group consisting of a reagent that detects ALK kinase activity, a reagent that detects a polypeptide with ALK kinase activity, and a reagent that detects to a polynucleotide encoding the polypeptide with ALK kinase activity, and (c) detecting reaction of the detection molecule with the biological sample, wherein reaction of the detection molecule with the biological sample indicates said polypeptide with ALK kinase activity is present or active in said mammalian kidney cancer or suspected mammalian kidney cancer.

In another aspect, the invention provides a method for identifying a mammalian kidney cancer or suspected mammalian kidney cancer that belongs to a subset of kidney cancers driven by ALK kinase activity, said method comprising the steps of (a) contacting a biological sample obtained from a mammalian kidney cancer or suspected mammalian kidney cancer with at least one detection molecule selected from the group consisting of a reagent that detects ALK kinase activity, a reagent that detects a polypeptide with ALK kinase activity, and a reagent that detects to a polynucleotide encoding the polypeptide with ALK kinase activity, and (b) detecting reaction of the detection molecule with said biological sample, wherein the reaction of the detection molecule with said biological sample indicates that said mammalian kidney cancer or suspected mammalian kidney cancer is driven by ALK kinase activity. In some embodiments, the mammalian kidney cancer or suspected mammalian kidney cancer driven by ALK kinase activity is likely to respond to a composition comprising at least one ALK-inhibiting therapeutic.

In another aspect, the invention provides method for determining whether a compound inhibits the progression of a mammalian kidney cancer or suspected mammalian kidney cancer driven by a polypeptide with ALK kinase activity, said method comprising the step of determining whether said compound inhibits the expression and/or activity of said polypeptide in said cancer mammalian kidney cancer or suspected mammalian kidney cancer.

In another aspect, the invention provides a method for inhibiting the progression of a mammalian kidney cancer or suspected mammalian kidney cancer driven by polypeptide with ALK kinase activity, comprising inhibiting the expression and/or activity of said polypeptide in said mammalian kidney cancer or suspected mammalian kidney cancer.

In another aspect, the invention provides a method for treating a mammalian patient with mammalian kidney cancer or suspected mammalian kidney cancer driven by a polypeptide with ALK kinase activity, said method comprising the step of administering a composition comprising a therapeutically effective amount of a composition comprising an ALK-inhibiting therapeutic to the mammalian patient.

In still a further aspect, the invention provides a method for treating a patient having a mammalian kidney cancer or suspected mammalian kidney cancer comprising the steps of: (a) detecting the presence or activity of said polypeptide with ALK kinase activity a biological sample of the mammalian kidney cancer or suspected mammalian kidney cancer of the patient; and (b) administering a composition comprising an ALK-inhibiting therapeutic to the patient. In some embodiments, the patient is a human.

As used herein, by "reaction" as in the reaction of the detection molecule with a biological sample is meant that the detection molecule is detecting its target in the biological sample. The nature of the reaction will, of course, depend upon the type of detection molecule used. The methods of the invention include the use of detection molecules that may be reagents that detect ALK kinase activity (e.g., a phosphotyrosine-specific antibody that detects phosphorylation of an ALK substrate or detecting autophosphorylation of ALK). In this case, detection of reaction may be made by detecting specific binding of the phosphotyrosine-specific antibody to the biological sample. The methods of the invention also include the use of detection molecules that may be reagents that detect a polypeptide with ALK kinase activity (e.g., an antibody that specifically binds the polypeptide). In this case, detection of reaction may be made by detecting specific binding of the polypeptide with ALK kinase activity-specific antibody to the biological sample. The methods of the invention also include the use of detection molecules that may be reagents that detect a polynucleotide that encodes a polypeptide with ALK kinase activity (e.g., a nucleic acid probe that hybridizes to an exonic or intronic sequence from a portion of the ALK gene that encodes the ALK kinase domain). In this case, detection of reaction may be made by detecting hybridization (e.g., under stringent conditions) of the probe to the biological sample.

The various aspects and embodiments of the invention are based on the discovery of ALK in cancerous cells in the kidney.

The term "ALK" refers to Anaplastic Lymphoma Kinase. ALK (Anaplastic Lymphoma Kinase) (GenBank accession Number: AB209477, UniProt Accession No. Q9UM73) is a receptor tyrosine kinase. This protein (which is 1620 amino acids long in humans) has a transmembrane domain in the central part and has a carboxyl-terminal tyrosine kinase region and an amino-terminal extracellular domain (Oncogene. 1997 Jan. 30; 14 (4): 439-49). See Pulford et al., Journal of Cellular Physiology, 199:330-358, 2004 for a comprehensive review relating to ALK. The full-length ALK sequence is disclosed in U.S. Pat. No. 5,770,421. In normal humans, full-length ALK protein expression has been detected in the brain and central nervous system, and has been reported in the small intestine and testis (see, e.g., Morris et al., Oncogene 14:2175-2188, 1997). The amino acid sequence of full length human ALK cDNA and protein is provided herein as SEQ ID NOs: 1 and 2, respectively. As shown in Table 1, the signal peptide, extracellular, transmembrane, and kinase domains of ALK are found at the following amino acid residues in SEQ ID NO: 2:

TABLE 1

| Domain | Amino acid residues in SEQ ID NO: 2 |
| --- | --- |
| Signal peptide | 1-18 |
| Extracellular domain | 19-1038 |
| Transmembrane domain | 1039-1059 |
| Cytoplasmic domain | 1060-1620 |
| Kinase domain | 1116-1392 |

The polypeptide sequence of exon 20 onward of the ALK is included herein as SEQ ID NO: 15. The polypeptide sequence of the ALK protein starting with the transmembrane domain and including the rest of the C'terminal portion of the protein is set forth in amino acid residues 1060-1620 of SEQ ID NO: 2.

The term "polypeptide" (or "amino acid sequence" or "protein") refers to a polymer formed from the linking, in a defined order, of preferably, α-amino acids, D-, L-amino acids, and combinations thereof. The link between one amino acid residue and the next is referred to as an amide bond or a peptide bond. Non-limiting examples of polypeptides include an oligopeptide, peptide, or protein sequence, and fragments or portions thereof, and naturally occurring or synthetic molecules (e.g., peptide synthesized by artificial means). Polypeptides also include derivatized molecules such as glycoproteins and lipoproteins as well as lower molecular weight polypeptides. "Amino acid sequence" and like terms, such as "polypeptide" or "protein", are not meant to limit the indicated amino acid sequence to the complete, naturally-occurring amino acid sequence associated with the recited polypeptide molecule. Accordingly, the term "polypeptide" also includes variants of the recited polypeptide that do not vary significantly from the structure or function of the recited polypeptide. If such differences in sequence are contemplated, it should be remembered that there will be critical areas on the protein which determine activity (e.g. the kinase domain of ALK polypeptide). In general, it is possible to replace residues that form the tertiary structure, provided that residues performing a similar function are used. In other instances, the type of residue may be completely unimportant if the alteration occurs at a non-critical region of the protein.

As used herein, the term "biological sample" refers to saliva, cells, mucous, tears, blood, serum, lymph/interstitial fluids, buccal cells, mucosal cells, cerebrospinal fluid, semen, feces, plasma, urine, marrow, a suspension of cells, or a suspension of cells and viruses or extracts or any of the foregoing, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support) obtainable from any mammal (e.g., a human), such as a normal mammal or a mammal having or suspected of having kidney cancer. In some embodiments, a biological sample is mammalian (e.g., human) and is a biopsy sample or a blood sample including a circulating tumor cell. Biological samples useful in the practice of the methods of the invention may be obtained from any mammal.

Any biological sample comprising cells (or extracts of cells) from a mammalian cancer is suitable for use in the methods of the invention. In one embodiment, the biological sample comprises cells obtained from a tumor biopsy. The biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., *Acta Cytol.* 36(3): 416-22 (1992)).

In some embodiments, the biological sample comprises circulating tumor cells. Circulating tumor cells ("CTCs") may be purified, for example, using the kits and reagents sold under the trademarks Vita-Assays™, Vita-Cap™, and CellSearch® (commercially available from Vitatex, LLC (a Johnson and Johnson corporation). Other methods for isolating CTCs are described (see, for example, PCT Publication No. WO/2002/020825, Cristofanilli et al., New Engl. J. of Med. 351 (8):781-791 (2004), and Adams et al., J. Amer. Chem. Soc. 130(27): 8633-8641 (July 2008)). In a particular embodiment, a circulating tumor cell ("CTC") may be isolated and identified as having originated from the kidney.

Accordingly, the invention provides a method for isolating a CTC, and then screening the CTC one or more assay formats to identify the presence of a polypeptide with ALK kinase activity a polynucleotide encoding the same in the CTC. Some non-limiting assay formats include Western blotting analysis, flow-cytometry (FC), immuno-histochemistry (IHC), immuno-fluorescence (IF), in situ hybridization (ISH), fluorescence in situ hybridization (FISH), and polymerase chain reaction (PCR). A CTC from a patient that is identified as comprising a polypeptide with ALK kinase activity or polynucleotide encoding the same may indicate that the patient's originating cancer (e.g., a kidney cancer such as an squamous kidney cancer cell or a granular kidney cancer cell) is likely to respond to a composition comprising at least one ALK kinase-inhibiting therapeutic.

Biological samples useful in the practice of the methods of the invention may be obtained from any mammal in which a cancer driven by polypeptide with ALK kinase activity is or might be present or developing.

In various embodiments, the mammal (e.g., from which the mammalian kidney cancer or suspected mammalian kidney cancer originates) is a human, and the human may be a candidate for an ALK-inhibiting therapeutic for the treatment of cancer driven by a polypeptide with ALK kinase activity. The human candidate may be a patient currently being treated with, or considered for treatment with, an ALK-inhibiting therapeutic or other kinase-inhibiting therapeutic (e.g., Tarceva®). In another embodiment, the mammal is large animal, such as a horse or cow, while in other embodiments, the mammal is a small animal, such as a dog or cat, all of which are known to develop kidney cancer.

Any biological sample comprising cells (or extracts of cells) from a mammalian cancer is suitable for use in the methods of the invention. In one embodiment, the biological sample comprises cells obtained from a tumor biopsy. The biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor by methods well known in the art (see Cristallini et al., *Acta Cytol.* 36(3): 416-22 (1992)).

Cellular extracts of the foregoing biological samples may be prepared, either crude or partially (or entirely) purified, in accordance with standard techniques, and used in the various methods of the invention. Alternatively, biological samples comprising whole cells may be utilized in assay formats such as immunohistochemistry (IHC), flow cytometry (FC), and immunofluorescence (IF), as further described herein. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

As used herein, by "polypeptide having ALK kinase activity" is meant any protein or polypeptide (or fusion or fragment thereof) that retains the signaling properties of a full length ALK protein (i.e., retains ALK kinase activity). Thus, polypeptides having ALK kinase activity include, without limitation, full-length ALK protein, portions of ALK comprising the kinase domain of ALK protein, truncated forms of ALK which retain ALK kinase activity (e.g., a truncated ALK polypeptide comprising the ALK kinase domain without the extracellular or transmembrane domain of full-length ALK) and all other ALK polypeptides, which may or may not be fused with other polypeptides, that retain their ALK biological activity and/or tyrosine kinase activity. ALK may be derived from any species, such as mammalian, including bovine, ovine, porcine, murine, equine, and human, and may be derived from any source whether natural, synthetic, semi-synthetic, or recombinant. The human full length ALK protein is set forth in SEQ ID NO:

2. Persons of skill in the art would be readily able to determine corresponding sequences in non-human mammalian ALK homologues.

In various embodiments of all of the aspects of the invention, the polypeptide with ALK kinase activity is aberrantly expressed full-length ALK protein.

By "aberrantly expressed full-length ALK polypeptide" is meant that full length ALK is expressed in a cell of the kidney or kidney tissue of a cancer or suspected cancer patient where, in the same cell or tissue type of a normal individual, full-length ALK is not expressed. Such aberrant expression may be due to, for example, mutations in regulatory sequences (such the promoter, enhancer, or intronic genomic sequences) operably linked to exons encoding amino acids of full-length ALK polypeptide which result in aberrant expression of full-length ALK polypeptide in the cell bearing the mutation. Numerous examples of aberrantly expressed ALK kinase have been found in other cancers. For example, point mutations within the kinase domain have been found in neuroblastoma and overexpression of ALK has been found in numerous cancers (including, e.g., retinoblastoma, breast cancer, and melanoma). See review in Palmer et al., Biochem. J. 420(3): 345-361 (May 2009), herein incorporated by reference in its entirety. Aberrant expression (e.g., overexpression) of full length ALK polypeptide in a cancer (e.g., a kidney cancer) may be the result of amplification of the ALK gene in the cancer cell's genome.

In various embodiments, the polypeptide with ALK kinase activity is an ALK fusion polypeptide comprising at least a portion of a first fusion member and at least a portion of a second fusion member, wherein the second fusion member is an ALK protein comprises an ALK kinase domain.

The term "ALK fusion polypeptide" refers to a portion or fragment of the ALK protein fused to at least a portion or fragment of another protein. In some embodiments, the portion of ALK protein present in an ALK fusion polypeptide comprises the kinase domain of full-length ALK protein. In some embodiments, the portions of the ALK present in an ALK fusion polypeptide comprise amino acids encoded by exon 20 onward of an ALK-encoding gene. In some embodiments, an ALK fusion polypeptide comprises the amino acid sequence set forth in SEQ ID NO: 3. In some embodiments, an ALK fusion polypeptide comprises the amino acid sequence set forth in SEQ ID NO: 4. In some embodiments, an ALK fusion polypeptide comprises the amino acid sequence set forth in SEQ ID NO: 15. An ALK fusion polypeptide often results from a chromosomal translocation or inversion. Non-limiting examples of ALK fusion polypeptides include VCL-ALK, EML4-ALK, NPM-ALK, TPM3-ALK, TFG-ALK, ATIC-ALK, CLTC-ALK, MSN-ALK, TPM4-ALK, ALO17-ALK, RANBP2-ALK, MYH9-ALK, CARS-ALK, SEC31L1-ALK, and KIF5B-ALK (see, e.g., Debelenko et al., Modern Pathology 24: 430-442, 2011; Marino-Enriquez et al., Genes, Chromosome, and Cancer 50(3): 146-153, 2011; Palmer et al., Biochem. J. 420(3): 345-361, 2009 (and the articles cited therein), Rikova et al., Cell 131: 1190-1203, 2007; Soda et al., Nature 448: 561-566, 2007; Morris et al., Science 263: 1281-1284, 1994; Du et al., J. Mol. Med 84: 863-875, 2007; Panagopoulos et al., Int. J. Cancer 118: 1181-1186, 2006; Cools et al., Genes Chromosomes Cancer 34: 354-362, 2002; Debelenko et al., Lab. Invest. 83: 1255-1265, 2003; Ma et al., Genes Chromosomes Cancer 37: 98-105, 2003; Lawrence et al., Am. J. Pathol. 157: 377-384, 2000; Hernandez et al., Blood 94: 3265-3268, 1999; Hernandez et al., Am J Pathol 160: 1487-1494, 2002; Takeuchi K., Clin Cancer Res. 15(9): 3143-3149, 2009; Tort et al., Lab. Invest. 81: 419-426, 2001; Trinei et al., Cancer Res. 60: 793-798, 2000; Colleoni et al., Am J Pathol. 156 (3): 781-9, 2000; Shiota et al, Blood 86: 1954-1960, 1995; Kuefer et al., Blood 90: 2901-2910, 1997; Shiota et al., Oncogene 9: 1567-1574, 1994; Touriol et al., Blood 95: 3204-3207, 2000; and Pulford et al., Journal of Cellular Physiology, 199:330-358, 2004. Some of these ALK fusions have multiple variants, all of which are considered ALK fusions and, thus, are included in the definition of mutant ALK of the invention. For example, there are multiple variants of TFG-ALK (see, e.g., Hernandez et al., Amer. J. Pathol. 160: 1487-1494, 2002) and at least nine known variants of EML4-ALK (see, e.g., Horn et al., J. of Clinical Oncology 27(26): 4232-4235, 2009, U.S. Pat. Nos. 7,728,120; 7,700,339 and EP Patent No. 1 914 240). Moreover, a method for identifying a protein as a fusion partner for ALK using ALK antibodies has been reported (Elenitoba-Johnson et al., Proc. Natl. Acad. Sci. 103: 7402-7407, 2006).

It should be noted that in all of the ALK fusion proteins described herein, the amino acid at the fusion junction (regardless of the numbering) may appear in either full-length protein member of the fusion, or the amino acid, being created by a codon with nucleotides from fused exons and/or of both protein members, may be unique to the fusion polypeptide and not appear in either full-length protein member of the fusion.

As used herein, a "portion" or "fragment" means a sequence fragment less than the whole sequence. For example, a 50 nucleotide sequence is a portion of a 100 nucleotide long sequence. Similarly, a 50 amino acid residue long sequence is a portion of a 100 amino acid long sequence. In some embodiments, a nucleic acid fragment or portion comprises at least 20 nucleotides, or at least 30 nucleotides, or at least 45 nucleotides, or at least 60 nucleotides, or at least 70 nucleotides, or at least 90 nucleotides. In some embodiments, a polypeptide fragment or portion comprises at least 6 amino acid residues, or at least 10 amino acid residues, or at least 20 amino acid residues, or at least 30 amino acid residues, or at least 45 amino acid residues, or at least 60 amino acid residues, or at least 70 amino acid residues, or at least 90 amino acid residues.

In one embodiment, the ALK fusion polypeptide contains the complete ALK tyrosine kinase domain located at amino acids 1116-1392 of ALK (SEQ ID NO: 3). In another embodiment, the ALK fusion polypeptide contains the complete intracytoplasmic domain located at amino acids 1060-1620 of ALK (SEQ ID NO: 4). In another embodiment, the ALK fusion polypeptide contains amino acid residues 1504-1507 (SEQ ID NO:5) of ALK making up the phosphotyrosine-binding site of the C-terminal domain of ALK. In yet another embodiment, the ALK fusion polypeptide contains amino acid residues 1603-1606 (SEQ ID NO:6) of ALK representing the interaction site for the phosphotyrosine-dependent binding of the substrate phospholipase C-γ (PLC-γ).

Because ALK is not known to be expressed in normal kidney cells, the presence or activity of a polypeptide with ALK kinase activity in mammalian kidney cancer or suspected mammalian kidney cancer is, in accordance with the invention, identified as a mammalian kidney cancer or suspected mammalian kidney cancer belonging to a subset of kidney cancers driven by ALK kinase activity.

As used herein, by "drive" or "driven" is meant that a mammalian kidney cancer or suspected mammalian kidney cancer has gained its cancerous state because of the presence within the cells of the mammalian kidney cancer or suspected mammalian kidney cancer of a polypeptide with ALK kinase activity. Such a presence may be detected by detecting the presence of a polynucleotide encoding the polypeptide with ALK kinase activity (e.g., detecting a gene translocation involving the ALK gene and another gene or detecting a mutation in the promoter of the ALK gene that would result in aberrant expression of full-length ALK polypeptide), detecting the polypeptide with ALK kinase activity, or by detecting ALK kinase activity of the polypeptide with ALK kinase activity. In other words, the presence of a polypeptide with ALK kinase activity stimulates or is the causative agent of the cancerous state of the mammalian kidney cancer or suspected mammalian kidney cancer.

As used herein, by "cancer" or "cancerous" is meant a cell that shows abnormal growth as compared to a normal (i.e., non-cancerous) cell of the same cell type. For example, a cancerous cell may be hyperplastic, anaplastic, metastatic, or benign (but shows abnormal growth). A cancerous cell may also show lack of contact inhibition where a normal cell of that same cell type shows contact inhibition.

In various embodiments of the invention, the activity of a polypeptide with ALK kinase activity is detected using as a detection molecule a reagent that detects ALK kinase activity.

Numerous reagents can be employed that detect ALK kinase activity. For example, substrates of ALK kinase are known (see, e.g., Donella-Deana et al., Biochemistry 44(23): 8533-8542, 2005; Simonitsch et al., FASEB J 15:1416-1418, 2001; and the Poly(Glu:Tyr)4:1 substrate commercially available from Sigma-Aldrich (St. Louis, Mo.; Catalog No. P-0275)). These substrates can be added to standard in vitro kinase assays and their phosphorylation on tyrosine determined (using, e.g., a phosphotyrosine-specific antibody such as the 4G10 antibody commercially available from Millipore, Bedford, Mass. or the P-Tyr-100 antibody (Catalog No. 9411) commercially available from Cell Signaling Technology, Inc., Danvers, Mass.

Note that because ALK autophosphorylates when its kinase activity is active (see Perez-Pinera et al., Journal of Biological Chemistry 282: 28683-28690, 207), the reagent that detects ALK kinase activity may itself be a phosphotyrosine-specific antibody that binds to tyrosine-phosphorylated ALK protein.

In some embodiments, ALK kinase activity is detected in an in vitro kinase assay format. In vitro kinase assays have been well known for many years (see, e.g., Ausubel et al., supra; Hernandez et al., Blood 94: 3265-3268, 1999). Indeed, in vitro kinase services for detecting ALK kinase activity are commercially available (from ProQinase GmbH, Freiburg, Germany).

In some embodiments, the method for detecting the presence and/or activity of a polypeptide with ALK kinase activity in a biological sample from a mammalian kidney cancer or suspected mammalian kidney cancer comprises the steps of: (a) obtaining a biological sample from a mammalian kidney cancer or suspected mammalian kidney cancer and (b) contacting the biological sample with a reagent that detects a polypeptide with ALK kinase activity, wherein detection of said polypeptide in said biological sample indicates said polypeptide with ALK kinase activity is present in said biological sample.

In various embodiments of the invention, the expression of a polypeptide with ALK kinase activity is detected using as a detection molecule a reagent that detects a polypeptide with ALK kinase activity. In some embodiments, the reagent specifically binds to a polypeptide with ALK kinase activity.

By "specifically binding" or "specifically binds" means that a reagent that may be used in the various methods of the invention (e.g., an antibody or AQUA peptide) interacts with its target molecule (e.g., a polypeptide with ALK kinase activity such as a full-length ALK polypeptide or a ALK fusion polypeptide), where the interaction is dependent upon the presence of a particular structure (e.g., the antigenic determinant or epitope on the polypeptide or the nucleotide sequence of the polynucleotide); in other words, the reagent is recognizing and binding to a specific polypeptide or polynucleotide structure rather than to all polypeptides or polynucleotides in general. By "binding fragment thereof" means a fragment or portion of a reagent that specifically binds the target molecule (e.g., an Fab fragment of an antibody).

A reagent that specifically binds to the target molecule may be referred to as a target-specific reagent or an anti-target reagent. For example, an antibody that specifically binds to a NPM-ALK polypeptide may be referred to as a NPM-ALK-specific antibody or an anti-NPM-ALK antibody. Likewise, an antibody that specifically binds to the full length ALK polypeptide may be referred to as an ALK-specific antibody or an anti-ALK antibody.

In some embodiments, a reagent that specifically binds its target molecule has a binding affinity ($K_D$) for its target molecule (e.g., an ALK fusion polypeptide) of $1 \times 10^{-6}$ M or less. In some embodiments, a reagent that specifically binds to its target molecule binds to its target molecule with a $K_D$ of $1 \times 10^{-7}$ M or less, or a $K_D$ of $1 \times 10^{-8}$ M or less, or a $K_D$ of $1 \times 10^{-9}$ M or less, or a $K_D$ of $1 \times 10^{-10}$ M or less, of a $K_D$ of $1 \times 10^{-11}$ M or less, of a $K_D$ of $1 \times 10^{-12}$ M or less. In certain embodiments, a reagent that specifically binds to its target molecule binds to its target molecule with a $K_D$ of 1 pM to 500 pM, or between 500 pM to 1 μM, or between 1 μM to 100 nM, or between 100 mM to 10 nM.

In some embodiments, a reagent that specifically binds to a polypeptide with ALK kinase activity is a heavy-isotope labeled peptide (i.e., an AQUA peptide). Such an AQUA peptide may be suitable for the absolute quantification of an expressed polypeptide with ALK kinase activity in a biological sample. As used herein, the term "heavy-isotope labeled peptide" is used interchangeably with "AQUA peptide". The production and use of AQUA peptides for the absolute quantification or detection of proteins (AQUA) in complex mixtures has been described. See PCT Publication No. WO/03016861 and also Gerber et al., *Proc. Natl. Acad. Sci. U.S.A.* 100: 6940-5 (2003). The term "specifically detects" with respect to such an AQUA peptide means the peptide will only detect and quantify polypeptides and proteins that contain the AQUA peptide sequence and will not substantially detect polypeptides and proteins that do not contain the AQUA peptide sequence.

AQUA internal peptide standards (heavy-isotope labeled peptides) may desirably be produced to detect any quantify any unique site (e.g., the fusion junction within an ALK fusion polypeptide) within a polypeptide with ALK kinase activity.

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al., supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g., trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g., 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known sequence previously identified by the IAP-LC-MS/MS method within in a target protein. If the site is modified, one AQUA peptide incorporating the modified form of the particular residue within the site may be developed, and a second AQUA peptide incorporating the unmodified form of the residue developed. In this way, the two standards may be used to detect and quantify both the modified an unmodified forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g., PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, in some embodiments, the peptide is not longer than about 20 amino acids. In some embodiments, the peptide is between about 7 to 15 amino acids in length. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e., the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are some non-limiting labels. Pairs of peptide internal standards that incorporate a different isotope label may also be prepared. Non-limiting amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g., an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a one non-limiting method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in PCT Publication No. WO/03016861 and Gerber et al. supra.

In some embodiments, a reagent that specifically binds to a polypeptide with ALK kinase activity is an antibody. In some embodiments, the antibody is specific for (i.e., specifically binds to) full length ALK polypeptide. In some embodiments, the antibody does not cross-react with (i.e., does not specifically bind to) c-Met. In some embodiments, the antibody is specific for the kinase domain of ALK. In some embodiments, the antibody is specific for the extracellular domain of ALK. In some embodiments, where the polypeptide with ALK kinase activity is an ALK fusion polypeptide, the antibody specifically binds to the portion of ALK polypeptide that is fused to the portion of ALK kinase present in the ALK fusion polypeptide. For example, if the fusion is EML4-ALK (the 796 variant), the antibody specifically binds to the portion of the ALK protein (e.g., the ALK kinase domain) present in the fusion. In some embodiments, where the polypeptide with ALK kinase activity is an ALK fusion polypeptide, the antibody specifically binds to the portion of the fusion partner that is fused to the portion of ALK kinase present in the ALK fusion polypeptide. For example, if the fusion is EML4-ALK (the 796 variant), the antibody specifically binds to the N-terminus of the EML4 protein present in the fusion.

The term "antibody" or "antibodies" refers to all types of immunoglobulins, including IgG, IgM, IgA, IgD, and IgE, including binding fragments thereof (i.e., fragments of an antibody that are capable of specifically binding to the antibody's target molecule, such as $F_{ab}$, and $F(ab')_2$ fragments), as well as recombinant, humanized, polyclonal, and monoclonal antibodies and/or binding fragments thereof. Antibodies of the invention can be derived from any species of animal, such as from a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Antibodies of the invention may be also be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to known methods (see, e.g., U.S. Pat. Nos. 4,474,893; 4,816,567; 7,485,291, and US Patent Publication No. 20110045534). The antibodies may also be chemically constructed specific antibodies made according to the method disclosed in U.S. Pat. No. 4,676,980.

Natural antibodies are the antibodies produced by a host animal, however the invention contemplates also genetically altered antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics. The term "humanized antibody", as used herein, refers to antibody molecules in which amino acids have been replaced in the non-antigen binding regions in order to more closely resemble a human antibody, while still retaining the original binding ability. Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies are also included in the present invention. These recombinant antibodies have the same amino acid sequence as the natural antibodies or have altered amino acid sequences of the natural antibodies. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety). Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203. The genetically altered antibodies of the invention may be functionally equivalent to the above-mentioned natural antibodies. In certain embodiments, modified antibodies of the invention provide improved stability or/and therapeutic efficacy.

Non-limiting examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of the invention can be modified post-translationally (e.g., acetylation, and/or phosphorylation) or can be modified synthetically (e.g., the attachment of a labeling group). Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions. The term "biologically active" refers to a protein having structural, regulatory, or biochemical functions of a naturally occurring molecule. Likewise, "immunologically active" refers to the capability of the natural, recombinant, or synthetic full-length ALK protein or ALK fusion polypeptide (e.g., a FN1-ALK fusion polypeptide or an FN1-tmALK fusion polypeptide of the invention), or any oligopeptide thereof, to induce a specific immune response in appropriate animals or cells and to bind with specific antibodies.

Also within the invention are antibody molecules with fewer than 4 chains, including single chain antibodies, Camelid antibodies and the like and components of an antibody, including a heavy chain or a light chain. In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region.

One non-limiting epitopic site of a ALK fusion polypeptide-specific antibody of the invention is a peptide fragment consisting essentially of about 11 to 17 amino acids of a fusion polypeptide sequence, which fragment encompasses the fusion junction between the ALK portion and the portion of the second fusion partner present in the ALK fusion polypeptide. It will be appreciated that antibodies that specifically binding shorter or longer peptides/epitopes encompassing the fusion junction of an ALK fusion polypeptide are within the scope of the present invention.

The invention is not limited to use of antibodies, but includes equivalent molecules, such as protein binding domains or nucleic acid aptamers, which bind, in a fusion-protein or truncated-protein specific manner, to essentially the same epitope to which a polypeptide with kinase activity-specific antibody useful in the methods of the invention binds. See, e.g., Neuberger et al., Nature 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired epitope (e.g. the fusion junction between the ALK portion and the portion of the second fusion partner present in the ALK fusion polypeptide), collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (Wiley and Sins, New York, N. Y. 1989 and yearly updates up to and including 2010). Monoclonal antibodies so produced are highly specific, and improve the selectivity and specificity of assay methods provided by the invention. For example, a solution containing the appropriate antigen (e.g. a synthetic peptide comprising the fusion junction of the ALK portion and the portion of the second fusion partner present in the ALK fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are desired for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, this method involves detecting or determining a sequence of monomers which is a topographical equivalent of a ligand which is complementary to the ligand binding site of a particular receptor of interest. Similarly, U.S. Pat. No. 5,480,971, Houghten et al. (1996) discloses linear $C_1$-C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and fusion protein specificity according to standard techniques. See, e.g., Czernik et al., *Methods in Enzymology,* 201: 264-283 (1991). For example, the antibodies may be screened against a peptide library by ELISA to ensure specificity for both the desired antigen and, if desired, for reactivity only with the full-length ALK protein, a particular ALK fusion polypeptide (e.g., an EML4-ALK (1059 amino acid variant) polypeptide), or fragments thereof of the invention. The antibodies may also be tested by Western blotting against cell preparations containing target protein to confirm reactivity with the only the desired target and to ensure no appreciable binding to other proteins. The production, screening, and use of fusion protein-specific antibodies is known to those of skill in the art, and has been described. See, e.g., U.S. Patent Publication No. 20050214301.

Full-length ALK protein-specific and ALK fusion polypeptide-specific antibodies useful in the methods of the invention may exhibit some limited cross-reactivity with similar epitopes in other proteins or polypeptides, such as similar fusion polypeptides. This is not unexpected as most antibodies exhibit some degree of cross-reactivity, and anti-peptide antibodies will often cross-react with epitopes having high homology or identity to the immunizing peptide. See, e.g., Czernik, supra. Cross-reactivity with other fusion proteins is readily characterized by Western blotting alongside markers of known molecular weight. Amino acid sequences of cross-reacting proteins may be examined to identify sites highly homologous or identical to full length ALK protein sequence or the ALK fusion polypeptide sequence to which the antibody binds. Undesirable cross-reactivity can be removed by negative selection using antibody purification on peptide columns.

Polypeptide with ALK kinase activity-specific antibodies and ALK fusion polypeptide-specific antibodies of the invention that are useful in practicing the methods disclosed herein are ideally specific for human fusion polypeptide, but are not limited only to binding the human species, per se. The invention includes the production and use of antibodies that also bind conserved and highly homologous or identical epitopes in other mammalian species (e.g., mouse, rat, monkey). Highly homologous or identical sequences in other species can readily be identified by standard sequence comparisons, such as using BLAST, with the human ALK protein sequence (SEQ ID NO: 2.

Antibodies employed in the methods of the invention may be further characterized by, and validated for, use in a particular assay format, for example flow cytometry (FC), immunohistochemistry (IHC), and/or immunocytochemistry (ICC). The use of polypeptide with ALK kinase activity-specific antibodies in such methods is further described herein. The antibodies described herein, used alone or in the below-described assays, may also be advantageously conjugated to fluorescent dyes (e.g. Alexa488, phycoerythrin), or labels such as quantum dots, for use in multi-parametric analyses along with other signal transduction (phospho-AKT, phospho-Erk 1/2) and/or cell marker (cytokeratin) antibodies, as further described below.

In practicing the methods of the invention, the expression and/or activity of a polypeptide with ALK kinase activity (e.g., a full-length ALK polypeptide) in a given biological sample may also be advantageously examined using antibodies specific for (i.e., that specifically bind to) full length ALK protein or antibodies specific for ALK fusion polypeptides. For example, ALK-specific antibodies (i.e., antibodies that specifically bind full-length ALK) are commercially available (see CELL SIGNALING TECHNOLOGY, INC., Danvers, Mass., Catalog Nos. 3333 and 3791; Abcam, 2010 Catalogue, #ab17127, ab59286, and Sigma-Aldrich, 2010 Catalog, #HPA010694, for example). In some embodiments, ALK-specific antibodies used in the methods of the invention specifically bind the cytoplasmic domain of ALK and, thus, will detect full-length ALK and ALK fusion polypeptides. In some embodiments, ALK-specific antibodies used in the methods of the invention specifically bind the kinase domain of ALK. Furthermore, ALK fusion-specific antibodies are commercially available (see CELL SIGNALING TECHNOLOGY, INC., Beverly Mass., 2009/10 Catalogue, #'s 33435 (phospho-NPM-ALK), 3983 (phospho-NPM-ALK), Abcam, 2010 Catalogue, #ab4061 (NPM-ALK), and Thermo Scientific, 2010 Catalogue, #PA1-37060 (NPM-ALK), for example). Such antibodies may also be produced according to standard methods, as described above.

Detection of expression and/or activity of full-length ALK and/or ALK fusion polypeptide in a biological sample (e.g. a tumor sample) can provide information on whether the fusion protein alone is driving the tumor, or whether aberrantly expressed full length ALK is also present and driving the tumor. Such information is clinically useful in assessing whether targeting the fusion protein or the full-length protein(s), or both, or is likely to be most beneficial in inhibiting progression of the tumor, and in selecting an appropriate therapeutic or combination thereof. Antibodies specific for the ALK kinase extracellular domain, which is not present in the mutant ALK disclosed herein, may be particularly useful for determining the presence/absence of the mutant ALK kinase.

It will be understood that more than one antibody may be used in the practice of the above-described methods. For example, one or more polypeptide with ALK kinase activity-specific antibodies together with one or more antibodies specific for full-length ALK kinase, another kinase, receptor, or kinase substrate that is suspected of being, or potentially is, activated in a cancer in which a polypeptide with ALK kinase activity is expressed and/or active may be simultaneously employed to detect the activity of such other signaling molecules in a biological sample comprising cells from such cancer.

Those of skill in the art will appreciate that fusion polypeptides of the present invention and the epitope-bearing fragments thereof described above can be combined with parts of other molecules to create chimeric polypeptides. For example, an epitope-bearing fragment of an ALK fusion polypeptide may be combined with the constant domain of immunoglobulins (IgG) to facilitate purification of the chimeric polypeptide and increase the in vivo half-life of the chimeric polypeptide (see, e.g., examples of CD4-Ig chimeric proteins in EPA 394,827; Traunecker et al., *Nature* 331: 84-86 (1988)). Fusion proteins that have a disulfide-linked dimeric structure (e.g., from an IgG portion may also be more efficient in binding and neutralizing other molecules than the monomeric ALK fusion polypeptide alone (see Fountoulakis et al., *J Biochem* 270: 3958-3964 (1995)).

In some embodiments, the detection molecule used in the methods of the invention is attached to a detectable label. By "detectable label" with respect to a polypeptide, polynucleotide, or reagent disclosed herein means a chemical, biological, or other modification of or to the polypeptide, polynucleotide, or binding agent, including but not limited to fluorescence, mass, residue, dye, radioisotope, label, or tag modifications, etc., by which the presence of the molecule of interest (e.g., a polypeptide with ALK kinase activity or a polynucleotide encoding a polypeptide with ALK kinase activity) may be detected. The detectable label may be directly or indirectly attached to the detection molecule by a covalent or non-covalent chemical bond. Methods for attaching detectable labels to molecules (e.g., to the detection molecules described herein) are well known.

Immunoassays useful in the practice of the methods of the invention may be homogenous immunoassays or heterogeneous immunoassays. In a homogeneous assay the immunological reaction usually involves a specific reagent (e.g., an ALK-specific antibody), a detectably labeled analyte, and the biological sample of interest. The signal arising from the detectable label is modified, directly or indirectly, upon the binding of the antibody to the detectably labeled analyte. Both the immunological reaction and detection of the extent thereof are carried out in a homogeneous solution. Immunochemical detectable labels that may be employed include free radicals, radio-isotopes, fluorescent dyes, enzymes, bacteriophages, coenzymes, and so forth. Semi-conductor nanocrystal labels, or "quantum dots", may also be advantageously employed, and their preparation and use has been well described. See generally, K. Barovsky, *Nanotech. Law & Bus.* 1(2): Article 14 (2004) and patents cited therein.

In a heterogeneous assay approach, the reagents are usually the biological sample, binding reagent (e.g., an antibody), and suitable means for producing a detectable signal. Biological samples as further described below may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. FN1-ALK fusion polypeptide-specific monoclonal antibodies may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of a protein with ALK kinase activity (e.g., a full-length ALK protein, a truncated ALK, or ALK fusion polypeptide) is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other binding reagents binding reagents may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Cell-based assays, such flow cytometry (FC), immunohistochemistry (IHC), immunocytochemistry (ICC), or immunofluorescence (IF) are particularly desirable in practicing the methods of the invention, since such assay formats are clinically-suitable, allow the detection of expression of a protein with ALK kinase activity (e.g., a mutant ALK polypeptide or an FN1-ALK fusion polypeptide) in vivo, and avoid the risk of artifact changes in activity resulting from manipulating cells obtained from, e.g. a tumor sample in order to obtain extracts. Accordingly, in some embodiments, the methods of the invention are implemented in a flow-cytometry (FC), immunocytochemistry (ICC), immuno-histochemistry (IHC), or immunofluorescence (IF) assay format.

Flow cytometry (FC) may be employed to determine the expression of polypeptide with ALK kinase activity in a mammalian tumor before, during, and after treatment with a drug targeted at inhibiting ALK kinase activity. For example, tumor cells from a fine needle aspirate may be analyzed by flow cytometry for expression and/or activation of a polypeptide with ALK kinase activity or polynucleotide encoding the same as well as for markers identifying cancer cell types, etc., if so desired. Flow cytometry may be carried out according to standard methods. See, e.g. Chow et al., *Cytometry* (*Communications in Clinical Cytometry*) 46: 72-78 (2001). Briefly and by way of example, the following protocol for cytometric analysis may be employed: fixation of the cells with 2% paraformaldehyde for 10 minutes at 37° C. followed by permeabilization in 90% methanol for 10 minutes on ice. Cells may then be stained with the primary antibody (e.g., a full-length ALK-specific or a ALK fusion polypeptide-specific antibody), washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed polypeptide with ALK kinase activity in the tumor. Similar analysis after treatment of the tumor with an ALK-inhibiting therapeutic would reveal the responsiveness of a polypeptide with ALK kinase activity-expressing tumor to the targeted inhibitor of ALK kinase.

Immunohistochemical (IHC) staining may be also employed to determine the expression and/or activation status of polypeptide with ALK kinase activity in a mammalian cancer (e.g., kidney cancer) before, during, and after treatment with a drug targeted at inhibiting ALK kinase activity (i.e., an ALK-inhibiting therapeutic). IHC may be carried out according to well-known techniques. See, e.g., ANTIBODIES: A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody (e.g., an ALK-specific or ALK fusion polypeptide-specific antibody) and secondary antibody; and finally detecting using ABC avidin/biotin method according to manufacturer's instructions.

Immunofluorescence (IF) assays may be also employed to determine the expression and/or activation status of a polypeptide with ALK kinase activity in a mammalian cancer before, during, and after treatment with a drug targeted at inhibiting ALK kinase activity. IF may be carried out according to well-known techniques. See, e.g., J. M. polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with a primary antibody against (i.e., that specifically binds to) a polypeptide with ALK kinase activity followed by a secondary antibody labeled with a fluorescent dye such as Alexa 488 and analyzed with an epifluorescent microscope.

A variety of other protocols, including enzyme-linked immunosorbent assay (ELISA), radio-immunoassay (RIA), and fluorescent-activated cell sorting (FACS), for measuring expression and/or activity of a polypeptide with ALK kinase activity are known in the art and provide a basis for diagnosing the presence of the polypeptide with ALK kinase activity (e.g., full-length ALK, truncated ALK, or an ALK fusion polypeptide such as an NPM-ALK fusion polypeptide). Normal or standard values for polypeptide with ALK kinase activity expression are established by combining body fluids or cell extracts taken from normal mammalian subjects, preferably human, with an antibody that specifically binds to the polypeptide with ALK kinase activity under conditions suitable for complex formation. The amount of standard complex formation may be quantified by various methods, but preferably by photometric means. Quantities of the polypeptide with ALK kinase activity expressed in subject (i.e., a patient) and control samples from biopsied tissues are compared with the standard values. Deviation between standard and subject values establishes the parameters for diagnosing disease. Of course, since the polypeptide with ALK kinase activity described herein are discovered in cancerous kidney cells, no biological samples of normal kidney tissue are expected to contain these polypeptide with ALK kinase activity or polynucleotides encoding the same.

In some embodiments, the method for detecting the presence and/or activity of a polypeptide with ALK kinase activity in a biological sample from a mammalian kidney cancer or suspected mammalian kidney cancer comprises the steps of: (a) obtaining a biological sample from a mammalian kidney cancer or suspected mammalian kidney cancer and (b) contacting the biological sample with a reagent that detects a polynucleotide encoding the polypeptide with ALK kinase activity, wherein detection of said polynucleotide in said biological sample indicates said polypeptide with ALK kinase activity is present in said biological sample.

As used herein, by "polynucleotide" (or "nucleotide sequence" or "nucleic acid molecule") refers to a polymer of individual nucleotides covalently joined together (e.g., via a phosphodiester bond). Thus, the definition includes, without limitation, DNA, RNA, genomic DNA, intronic DNA, exonic DNA, cDNA, hnRNA, mRNA, oligonucleotides, or synthetic nucleotides, all of which may be single- or double-stranded, and may represent the sense or anti-sense strand. Probes and primers are within the definition of polynucleotides of the invention.

As used herein, by "polynucleotide encoding a polypeptide with ALK kinase activity" is meant to include, without limitation, any polynucleotide encoding a polypeptide with ALK kinase activity, any polynucleotide encoding a portion of a polypeptide with ALK kinase activity (e.g., the ALK kinase domain), and any polynucleotide from a gene encoding a polypeptide with ALK kinase activity regardless of whether that particular polynucleotide codes for any amino acid residues in that polypeptide with ALK kinase activity. For example, intronic sequences from an ALK gene (e.g., from an intron separating two exons coding for portions of the ALK kinase domain) are included in the definition of polynucleotide encoding a polypeptide with ALK kinase activity.

The nucleotide sequences, including cDNA and mRNA, of polynucleotides encoding polypeptides with ALK kinase activity have been previously published. Non-limiting examples include the nucleotide and protein sequences of human ALK (Genbank Accession Codes: U62540, U66559), the nucleotide and protein sequences of mouse ALK cDNAs (D83002), nucleotide and polypeptide sequences for EML4-ALK (U.S. Pat. No. 7,605,131), EML4-ALK (U.S. Pat. No. 7,700,339), EML4-ALK (GenBank AB462412.1), EML4-ALK (GenBank AB462411.1), KIF5B-ALK (GenBank AB462413.1), and TFG-ALK (GenBank AF143407.1). Furthermore, K. Pulford et al., *Anaplastic Lymphoma Kinase Proteins in Growth Control and Cancer*, J. Cell. Physiol. 199, 330-358 (2004) discloses other publicly available ALK fusion polypeptides.

In various embodiments of all of the aspects of the invention, the reagent that detects a polynucleotide encoding the polypeptide with ALK kinase activity is a nucleic acid probe or primer that hybridizes to said polynucleotide. In some embodiments, the nucleic acid probe or primer hybridizes to the polynucleotide encoding the polypeptide with ALK kinase activity under stringent conditions.

As used herein, by "probe," "primer," or "oligonucleotide" is meant a single-stranded nucleic acid molecule of defined sequence that can base-pair to a second DNA or RNA molecule that contains a complementary sequence (the "target"). The target is generally a nucleic acid ALK gene product of an ALK fusion gene. The stability of the resulting hybrid depends upon the extent of the base-pairing that occurs. The extent of base-pairing is affected by parameters such as the degree of complementarity between the probe and target molecules, and the degree of stringency of the hybridization conditions. The degree of hybridization stringency is affected by parameters such as temperature, salt concentration, and the concentration of organic molecules such as formamide, and is determined by methods known to one skilled in the art.

Probes or primers that specifically bind to a polynucleotide encoding a polypeptide having ALK kinase activity (or a portion of such a polynucleotide) specifically bind the polynucleotide by hybridizing to the polynucleotide. To do this, the probe or primer that specifically binds (e.g., hybridizes) to the polynucleotide encoding a polypeptide having ALK kinase activity (or a fragment of such a polynucleotide) preferably has at least 50%-55% sequence complementarity, more preferably at least 60%-75% sequence complementarity, even more preferably at least 80%-90% sequence complementarity, yet more preferably at least 91%-99% sequence complementarity, and most preferably 100% sequence complementarity to the polynucleotide encoding a polypeptide having ALK kinase activity (or a fragment of such a polynucleotide) to be detected. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

As used herein, by "hybridizes" is meant that a probe, primer, or oligonucleotide recognizes and physically interact (i.e., forms base-pairs) with a substantially complementary nucleic acid (e.g., an mRNA encoding full-length ALK or an ALK fusion polypeptide of the invention) under stringent conditions, and does not substantially base pair with other nucleic acids. A nucleic acid probe, primer, or oligonucleotide that hybridizes under stringent conditions to its target may be referred to as a target-specific nucleic acid probe (or primer or oligonucleotide) or an anti-target nucleic acid probe (or primer or oligonucleotide). For example, a nucleic acid probe that hybridizes to a polynucleotide encoding an EML4-ALK fusion polypeptide may be referred to as an EML4-ALK-specific nucleic acid probe or an anti-EML4-ALK nucleic acid probe.

As used herein, the term "stringent conditions" with respect to nucleotide sequence or nucleotide probe hybridization conditions is the "stringency" that occurs within a range from about $T_m$ minus 5° C. (i.e., 5° C. below the melting temperature ($T_m$) of the reagent or nucleic acid probe) to about 20° C. to 25° C. below $T_m$. Typical stringent conditions are: overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences. For example, for a DNA probe of at least 500 nucleotides in length, stringent conditions may be achieved by hybridization occurring in a buffer containing 0.5 M $NaHPO_4$, pH 7.2, 7% SDS, 1 mM EDTA, and 1% BSA (fraction V), at a temperature of 65° C., or a buffer containing 48% formamide, 4.8×SSC, 0.2 M Tris-Cl, pH 7.6, 1x Denhardt's solution, 10% dextran sulfate, and 0.1% SDS, at a temperature of 42° C. (or similarly typical conditions for stringenct Northern or Southern hybridizations). Stringent hybridization is relied upon for the success of numerous techniques routinely performed by molecular biologists, such as high stringency PCR, DNA sequencing, single strand conformational polymorphism analysis, and in situ hybridization. In contrast to Northern and Southern hybridizations, these techniques are usually performed with relatively short probes (e.g., usually 16 nucleotides or longer for PCR or sequencing, and 40 nucleotides or longer for in situ hybridization). The stringent conditions used in these techniques are well known to those skilled in the art of molecular biology, and may be found, for example, in F. Ausubel et al., *Current Protocols in Molecular Biology*, supra, herein incorporated by reference.

In various embodiments of all of the aspects of the invention, the nucleic acid probe or primer is a polymerase chain reaction (PCR) probe, a fluorescence in situ hybridization (FISH) probe, or a Southern blotting probe. In some embodiments, the method is implemented in a polymerase chain reaction (PCR) assay format, a in situ hybridization (ISH) assay format, or a Southern blotting assay format.

Polynucleotides encoding a polypeptide with ALK kinase activity may also be used for diagnostic purposes. The polynucleotides that may be used include oligonucleotide sequences, antisense RNA and DNA molecules, and PNAs. The polynucleotides may be used to detect and quantitate gene expression in biopsied tissues in which expression of a polypeptide with ALK kinase activity (e.g., full length ALK, or an ALK fusion polypeptide, The diagnostic assay may be used to distinguish between absence, presence, and aberrant expression of a polypeptide with ALK kinase activity, and to monitor regulation of levels of a polypeptide with ALK kinase activity during therapeutic intervention.

In one embodiment, hybridization with PCR probes which are capable of detecting a polynucleotide, including genomic sequences, encoding a polypeptide with ALK kinase activity may be used to identify polynucleotides that encode such polypeptides with ALK kinase activity. The construction and use of such probes is described herein. The specificity of the probe, whether it is made from a highly specific region, e.g., 10 unique nucleotides in the fusion junction, or a less specific region, e.g., the 3' coding region, and the degree of the hybridization or amplification (e.g., stringent hybridization or not stringent) will determine whether the probe identifies only naturally occurring sequences encoding mutant ALK kinase polypeptide, alleles, or related sequences. In some embodiments, nucleic acid probes useful in the methods described herein may hybridize to nucleotide sequences encoding the kinase domain of ALK (amino acids 1116-1392 of SEQ ID NO:2). The probes may alternatively hybridize nucleotides encoding the C-terminal domain located at amino acids 1376-1620 of SEQ ID NO: 2, amino acid residues 1504-1507 of SEQ ID NO:2 making up the phosphotyrosine-binding site of the C-terminal domain of ALK, or amino acid residues 1603-1606 of SEQ ID NO: 2 representing the interaction site for the phosphotyrosine-dependent binding of the substrate phosphlipase C-γ (PLC-γ).

In another embodiment of the invention, the polynucelotides encoding a polypeptide with ALK kinase activity may be used to generate hybridization probes which are useful for mapping the naturally occurring genomic sequence. The sequences may be mapped to a particular chromosome or to a specific region of the chromosome using well known techniques. Such techniques include in-situ hybridization (ISH), FACS, or artificial chromosome constructions, such as yeast artificial chromosomes, bacterial artificial chromosomes, bacterial P1 constructions or single chromosome cDNA libraries, as reviewed in Price, C. M., *Blood Rev.* 7: 127-134 (1993), and Trask, B. J., *Trends Genet.* 7: 149-154 (1991).

In situ hybridization (ISH) of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti et al., *Nature* 336: 577-580 (1988)), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In one embodiment, fluorescence in-situ hybridization (FISH) (a non-limiting type of in situ hybridization assay) is employed (as described in Verma et al. HUMAN CHROMOSOMES: A MANUAL OF BASIC TECHNIQUES, Pergamon Press, New York, N.Y. (1988)) and may be correlated with other physical chromosome mapping techniques and genetic map data. The FISH technique is well known (see, e.g., U.S. Pat. Nos. 5,756,696; 5,447,841; 5,776,688; and 5,663,319). Examples of genetic map data can be found in the 1994 Genome Issue of *Science* (265: 19810. Correlation between the location of the gene encoding ALK protein and/or the gene encoding the fusion partner of an ALK fusion polypeptide on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals. FISH protocols for detect translocations involving the ALK gene have been described (see, e.g., U.S. Pat. No. 7,700,339 and US Patent Publication No. 20110110923. A dual color, break apart probe designed to detect ALK gene translocation is also commercially available from Abbott Molecular (Abbott Park, Ill., US; Catalog No. 05J89-001).

It shall be understood that all of the methods (e.g., PCR and FISH) that detect a polynucleotide encoding a polypeptide with ALK kinase activity may be combined with other methods that detect expression and/or activity of a polypeptide with ALK kinase activity. For example, detection of a polynucleotide encoding an ALK fusion polypeptide in the genetic material of a biological sample (e.g., TFG-ALK in a circulating tumor cell) may be followed by Western blotting analysis or immuno-histochemistry (IHC) analysis of the proteins of the sample to determine if the polynucleotide encoding the TFG-ALK fusion polypeptide is actually expressed as a TFG-ALK fusion polypeptide in the biological sample. Such Western blotting or IHC analyses may be performed using an antibody that specifically binds to the polypeptide encoded by the detected polynucleotide, or the analyses may be performed using antibodies that specifically bind either to full length TFG (e.g., bind to the N-terminus of the TFG protein) or to full length ALK (e.g., bind an epitope in the kinase domain of ALK protein). Such assays are known in the art (see, e.g., U.S. Pat. No. 7,468,252).

In another example, the CISH technology of Dako allows chromatogenic in situ hybridization with immuno-histochemistry on the same tissue section. See Elliot et al., Br J Biomed Sci 2008; 65(4): 167-171, 2008 for a comparison of CISH and FISH.

In another aspect, the invention relates to detecting the detection molecules utilizing a detection device. By "detection device" is meant any device that is used to detect, measure, or otherwise quantify the expression and/or activity levels of the polypeptide with ALK kinase activity or polynucleotide encoding the polypeptide with ALK kinase activity. The detected levels of expression and/or activity may be used to generate a database of the samples, particularly of the test and control samples. The database can be used to generate a report to analyze and compare the levels of expression and/or activity of the polypeptide with ALK kinase activity or polynucleotide encoding the polypeptide with ALK kinase activity of the samples. Non-limiting examples of detection devices include a PCR cycler, DNA analyzer, DNA sequencer, DNA extraction column, gel, or kit, image analysis device, chromatographic device, or mass spectrometer, combinations thereof, and automated versions thereof. An image analysis device is any device that is used to create a visible image of the biological sample for detection of the polypeptide with ALK kinase activity or polynucleotide encoding the polypeptide with ALK kinase activity and includes the following non-limiting examples: FlowCAM, a biosensor imaging device, an infrared imaging systems, or a chemiluminescent imaging systems. A chromatographic device may alternatively be used to detect the ALK gene product, which can perform high performance liquid chromatography (HPLC), reverse HPLC, gas chromatography, or liquid chromatography. In another embodiment, a mass spectrometer may be utilized.

In one embodiment, polypeptide with ALK kinase activity or polynucleotide encoding the polypeptide with ALK kinase activity are detected in a biological sample using a mass spectrometer. The term "mass spectrometer" (MS) means a device capable of detecting specific molecular species and measuring their accurate masses. The term is meant to include any molecular detector into which a polypeptide or peptide may be eluted for detection and/or characterization and includes, for example, MALDI and SELDI devices. In the preferred MS procedure, a sample, e.g., the elution solution, is loaded onto the MS instrument, and undergoes vaporization. The components of the sample are ionized by one of a variety of methods (e.g., by electrospray ionization or "ESI"), which results in the formation of positively charged particles (ions). The positive ions are then accelerated by a magnetic field. The computation of the mass-to-charge ratio of the particles is based on the details of motion of the ions as they transit through electromagnetic fields, and detection of the ions. The preferred mass measurement error of a mass spectrometer of the invention is 10 ppm or less, more preferable is 7 ppm or less; and most preferably 5 ppm or less.

Fragment ions in the MS/MS and MS$^3$ spectra are generally highly specific and diagnostic for peptides of interest. In contrast, to prior methods, the identification of peptide diagnostic signatures provides for a way to perform highly selective analysis of a complex protein mixture, such as a cellular lysate in which there may be greater than about 100, about 1000, about 10,000, or even about 100,000 different kinds of proteins. Thus, while conventional mass spectroscopy would not be able to distinguish between peptides with different sequences but similar m/z ratios (which would tend to co-elute with any labeled standard being analyzed), the use of peptide fragmentation methods and multistage mass spectrometry in conjunction with LC methods, provide a way to detect and quantify target proteins which are only a small fraction of a complex mixture (e.g., present in less than 2000 copies per cell or less than about 0.001% of total cellular protein) through these diagnostic signatures.

Test peptides in a biological sample are preferably examined by monitoring of a selected reaction in the mass spectrometer. This involves using the prior knowledge gained by the characterization of a standard peptide and then requiring the mass spectrometer to continuously monitor a specific ion in the MS/MS or MS$''$ spectrum for both the peptide of interest and the standard peptide. After elution, the areas-under-the-curve (AUC) for both the standard peptide and target peptide peaks may be calculated. The ratio of the two areas provides the absolute quantification that may then be normalized for the number of cells used in the analysis and the protein's molecular weight, to provide the precise number of copies of the protein per cell.

As used herein the term, "accurate mass" refers to an experimentally or theoretically determined mass of an ion that is used to determine an elemental formula. For ions containing combinations of the elements C, H, N, O, P, S, and the halogens, with mass less than 200 Unified Atomic Mass Units, a measurement about 5 ppm uncertainty is sufficient to uniquely determine the elemental composition.

As used herein the term, "predetermined peptide accurate mass" refers to the experimentally determined or calculated accurate mass of a peptide with a known amino acid sequence (along with any associated post-translational modifications). The accurate mass of any such specific amino acid sequence may be readily calculated by one of skill in the art.

As used herein, "a peptide fragmentation signature" refers to the distribution of mass-to-charge ratios of fragmented peptide ions obtained from fragmenting a peptide, for example, by collision induced disassociation, ECD, LID, PSD, IRNPD, SID, and other fragmentation methods. A peptide fragmentation signature which is "diagnostic" or a "diagnostic signature" of a target protein or target polypeptide is one which is reproducibly observed when a peptide digestion product of a target protein/polypeptide identical in sequence to the peptide portion of a standard peptide, is fragmented and which differs only from the fragmentation pattern of the standard peptide by the mass of the mass-altering label and/or the presence of a ubiquitin remnant. Preferably, a diagnostic signature is unique to the target protein (i.e., the specificity of the assay is at least about 95%, at least about 99%, and preferably, approaches 100%).

In some embodiments, the mammalian kidney cancer or suspected mammalian kidney cancer in which the presence or activity of said polypeptide with ALK kinase activity is detected is identified as a mammalian kidney cancer or suspected mammalian kidney cancer likely to respond to an ALK-inhibiting therapeutic.

As used herein, by "likely to respond" is meant that a cancer is more likely to show growth retardation or growth abrogation in response to (e.g., upon contact with or treatment by) an ALK inhibitor (also referred to as an ALK-inhibiting therapeutic) as compared to an untreated cancer (e.g., of the same tissue type as the treated cancer). In some embodiments, a cancer that is likely to respond to an ALK inhibitor is one that shrinks in size (e.g., the cancer cells apoptose) in response to the ALK inhibitor as compared to an untreated cancer. In some embodiments, a cancer that is likely to respond to an ALK inhibitor is one that dies (e.g., the cancer cells apoptose) in response to the ALK inhibitor as compared to an untreated cancer.

Accordingly, should a patient or subject whose kidney cancer or suspected kidney cancer is identified as comprising a polypeptide with ALK kinase activity (e.g., by detection of ALK kinase activity, a polypeptide with ALK kinase activity, and/or a polynucleotide encoding a polypeptide with ALK kinase activity), that patient may be treated with (e.g., administered with) a therapeutically effective amount of an ALK-inhibiting therapeutic. In some embodiments, the ALK-inhibiting therapeutic is administered in a pharmaceutically acceptable formulation.

As used herein, by "therapeutically effective amount" or "pharmaceutically effective amount" is mean an amount of an ALK-inhibiting therapeutic that is adequate to inhibit the cancer (or cell thereof) or suspected cancer (or cells thereof), as compared to an untreated cancer or suspected cancer, by either slowing the growth of the cancer or suspected cancer, reducing the mass of the cancer or suspected cancer, reducing the number of cells of the cancer or suspected cancer, or killing the cancer.

An ALK-inhibiting therapeutic may be any composition comprising at least one ALK inhibitor. Such compositions also include compositions comprising only a single ALK-inhibiting compound, as well as compositions comprising multiple therapeutics (including those against other RTKs), which may also include a non-specific therapeutic agent like a chemotherapeutic agent or general transcription inhibitor.

In some embodiments, an ALK-inhibiting therapeutic useful in the practice of the methods of the invention is a targeted, small molecule inhibitor. Small molecule targeted inhibitors are a class of molecules that typically inhibit the activity of their target enzyme by specifically, and often irreversibly, binding to the catalytic site of the enzyme, and/or binding to an ATP-binding cleft or other binding site within the enzyme that prevents the enzyme from adopting a conformation necessary for its activity.

Crizotinib (also known as PF-02341066 or 1066), is a c-MET/HGFR and ALK (anaplastic lymphoma kinase) inhibitor of the aminopyridine chemical series that is being developed by Pfizer Incorporated (see Zou et al., Cancer Research 67: 4408-4417, 2007 and supplemental data). Crizotinib is currently undergoing clinical trials testing its safety and efficacy in treating several forms of cancer, particularly non-small cell lung carcinoma (NSCLC), anaplastic large cell lymphoma, neuroblastoma, and other advanced solid tumors in both adults and children.

U.S. Pub. No. 2008/0300273 discloses that PF-02341066 was able to reduce cell colony scattering in HGF-stimulated Madin-Darby Canine Kidney (MDCK) cells. As such, the compound was able to inhibit epithelial cell dispersion and motility in response to HGF. See also Zou et al., Cancer Research 67: 4408-4417, 2007. However, these publications do not disclose whether or not ALK or ALK fusions are actually expressed in kidney cells or kidney cancer cells. In fact, Zou et al., Cancer Research 67: 4408-4417, 2007 references Christensen et al., Cancer Res. 63: 7345, 2003 as describing a cMET-inhibiting assay using the MDCK cell model. To determine whether or not HGF-stimulated MDCK cells actually express ALK kinase, the present inventors replicated the conditions described in U.S. Pub. No. 2008/0300273. As described below in Example 3, using Western blotting analysis, it was determined that HGF-stimulated MDCK cells do not express any ALK kinase. The cells did not express phosphorylated or non-phosphorylated ALK kinase. Accordingly, the effects on HGF-stimulated MDCK cells in response to crizotinib described in U.S. Pub. No. 2008/0300273 could not have been mediated by the ALK kinase since ALK kinase was not present in the cells. Accordingly, as proposed in U.S. Pub. No. 2008/0300273, the effects of crizotinib on HGF-stimulated MDCK cells were mediated through MET kinase.

Additional small molecule kinase inhibitors that may target ALK include TAE-684 (from Novartis; see Galkin, et al., Proc. National Acad. Sci 104(1) 270-275, 2007), AP26113 (Ariad Pharmaceuticals, Inc.), and CEP-14083, CEP-14513, and CEP-11988 (Cephalon; see Wan et al., Blood 107: 1617-1623, 2006); and WHI-P131 and WHI-P154 (EMD Biosciences; see Marzec et al., (Laboratory Investigation: A journal of Technical Methods and Pathology 2005, Vol. 85, p. 1544-1554, 2005). Another group has developed their own low-molecular-weight ALK-inhibiting substance and has demonstrated that this inhibitor induces the cell death of NPM-ALK-expressing lymphoma cell lines (Blood, 2006, Vol. 107, p. 1617-1623). In addition, numerous other compounds having an inhibitory activity against ALK have been reported including 5-chloro-$N^4$-[2-(isopropylsulfonyl)phenyl]-$N_2$-{2-methoxy-4-[4-(4-methylpiperazin-1-yl)piperidin-1-yl]phenyl}pyrimidine-2,4-diamine and 2-[(5-bromo-2-{[2-methoxy-4-(4-methylpiperazin-1-yl)phenyl]amino}pyrimidi-n-4-yl)amino]-N-methylbenzenesulfonamide (see Mosse et al., Clin Cancer Res. 2009 Sep. 15; 15(18):5609-14, 2009; Journal of Medicinal Chemistry 49: 1006-1015, 2006; Cancer Research, (US), 2004, Vol. 64, p. 8919-8923, 2004; Proc. Natl Acad. Sci. 101:13306-13311, 2004; Annual Review of Medicine, (US) 54: 73, 2003; Laboratory Investigation; A Journal of Technical Methods and Pathology, (US) 83: 1255-1265, 2003; Cellular and Molecular Life Sciences 61: 2897-2911, 2004; Science 278: 1309-1312, 1997; Oncogene 14 (4): 439-449, 1997; Oncogene 9: 1567-1574, 1994; Am J Pathol 160: 1487-1494, 2002; Am J Pathol 157: 377-384, 2000; Blood 90: 2901-2910, 1997; Am J Pathol. 156 (3): 781-9, 2000; J Comb Chem. 8: 401-409, 2006 and U.S. Pub. Nos. 20100152182; 20100099658; 20100048576; 20090286778; 20090221555; 20090186801; 20090118216; 20090099193; 20080176881; 20080090776; 2008/0300273; WO 2005/097765; WO 2005/009389; WO 2005/016894; WO 2004/080980; and WO2004079326.

Additional small molecule inhibitors and other inhibitors (e.g., indirect inhibitors) of ALK kinase activity may be rationally designed using X-ray crystallographic or computer modeling of ALK three dimensional structure, or may found by high throughput screening of compound libraries for inhibition of key upstream regulatory enzymes and/or necessary binding molecules, which results in inhibition of ALK kinase activity. Such approaches are well known in the art, and have been described. ALK inhibition by such therapeutics may be confirmed, for example, by examining the ability of the compound to inhibit ALK activity, but not other kinase activity, in a panel of kinases, and/or by examining the inhibition of ALK activity in a biological sample comprising cancer cells (e.g., kidney cancer cells). Methods for identifying compounds that inhibit a cancer characterized by the expression/presence of polypeptide with ALK kinase activity, are further described below.

ALK-inhibiting therapeutics useful in the methods of the invention may also be targeted antibodies that specifically bind to critical catalytic or binding sites or domains required for ALK activity, and inhibit the kinase by blocking access of ligands, substrates or secondary molecules to a and/or preventing the enzyme from adopting a conformation necessary for its activity. The production, screening, and therapeutic use of humanized target-specific antibodies has been well-described. See Merluzzi et al., *Adv Clin Path.* 4(2): 77-85 (2000). Commercial technologies and systems, such as Morphosys, Inc.'s Human Combinatorial Antibody Library (HuCAL®), for the high-throughput generation and screening of humanized target-specific inhibiting antibodies are available.

The production of various anti-receptor kinase targeted antibodies and their use to inhibit activity of the targeted receptor has been described. See, e.g. U.S. Patent Publication No. 20040202655, U.S. Patent Publication No. 20040086503, U.S. Patent Publication No. 20040033543, Standardized methods for producing, and using, receptor tyrosine kinase activity-inhibiting antibodies are known in the art. See, e.g., European Patent No. EP1423428, Phage display approaches may also be employed to generate ALK-specific antibody inhibitors, and protocols for bacteriophage library construction and selection of recombinant antibodies are provided in the well-known reference text CURRENT PROTOCOLS IN IMMUNOLOGY, Colligan et al. (Eds.), John Wiley & Sons, Inc. (1992-2000), Chapter 17, Section 17.1. See also U.S. Pat. Nos. 6,319,690, 6,300,064, 5,840, 479, and U.S. Patent Publication No. 20030219839.

ALK-binding targeted antibodies identified in screening of antibody libraries as describe above may then be further screened for their ability to block the activity of ALK, both in vitro kinase assay and in vivo in cell lines and/or tumors. ALK inhibition may be confirmed, for example, by examining the ability of such antibody therapeutic to inhibit ALK kinase activity in a panel of kinases, and/or by examining the inhibition of ALK activity in a biological sample comprising cancer cells, as described above. In some embodiments, a ALK-inhibiting compound of the invention reduces ALK kinase activity, but reduces the kinase activity of other kinases to a lesser extent (or not at all). Methods for screening such compounds for ALK kinase inhibition are further described above.

ALK-inhibiting compounds that useful in the practice of the disclosed methods may also be compounds that indirectly inhibit ALK activity by inhibiting the activity of proteins or molecules other than ALK kinase itself. Such inhibiting therapeutics may be targeted inhibitors that modulate the activity of key regulatory kinases that phosphorylate or de-phosphorylate (and hence activate or deactivate) ALK itself, or interfere with binding of ligands. As with other receptor tyrosine kinases, ALK regulates downstream signaling through a network of adaptor proteins and downstream kinases. As a result, induction of cell growth and survival by ALK activity may be inhibited by targeting these interacting or downstream proteins.

ALK kinase activity may also be indirectly inhibited by using a compound that inhibits the binding of an activating molecule necessary for full length ALK, an ALK fusion polypeptide (e.g., an FN1-ALK fusion polypeptide), or mutant ALK (e.g., a truncated ALK polypeptide or an FN1-tmALK fusion polypeptide) to adopt its active conformation. For example, the production and use of anti-PDGF antibodies has been described. See U.S. Patent Publication No. 20030219839, "Anti-PDGF Antibodies and Methods for Producing Engineered Antibodies," Bowdish et al. Inhibition of ligand (PDGF) binding to the receptor directly down-regulates the receptor activity.

ALK inhibiting compounds or therapeutics may also comprise anti-sense and/or transcription inhibiting compounds that inhibit ALK kinase activity by blocking transcription of the gene encoding ALK, an FN1-ALK fusion-encoding gene, or a mutant ALK-encoding gene. The inhibition of various receptor kinases, including VEGFR, EGFR, and IGFR, and FGFR, by antisense therapeutics for the treatment of cancer has been described. See, e.g., U.S. Pat. Nos. 6,734,017; 6,710,174, 6,617,162; 6,340,674; 5,783,683; 5,610,288.

Antisense oligonucleotides may be designed, constructed, and employed as therapeutic agents against target genes in accordance with known techniques. See, e.g. Cohen, J., *Trends in Pharmacol. Sci.* 10(11): 435-437 (1989); Marcus-Sekura, *Anal. Biochem.* 172: 289-295 (1988); Weintraub, H., *Sci. AM* pp. 40-46 (1990); Van Der Krol et al., *BioTechniques* 6(10): 958-976 (1988); Skorski et al., *Proc. Natl. Acad. Sci. USA* (1994) 91: 4504-4508. Inhibition of human carcinoma growth in vivo using an antisense RNA inhibitor of EGFR has recently been described. See U.S. Patent Publication No. 20040047847. Similarly, a ALK-inhibiting therapeutic comprising at least one antisense oligonucleotide against a mammalian ALK gene, FN1-ALK fusion polynucleotide or mutant ALK polynucleotide may be prepared according to methods described above. Pharmaceutical compositions comprising ALK-inhibiting antisense compounds may be prepared and administered as further described below.

Small interfering RNA molecule (siRNA) compositions, which inhibit translation, and hence activity, of ALK through the process of RNA interference, may also be desirably employed in the methods of the invention. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, U.S. Patent Publication No. 20020086356, and U.S. Patent Publication 20040229266.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available (e.g., Promega, Inc.; and Dharmacon, Inc. Detailed technical manuals on the design, construction, and use of dsRNA for RNAi are available. See, e.g., Dharmacon's "RNAi Technical Reference & Application Guide"; Promega's "RNAi: A Guide to Gene Silencing." ALK-inhibiting siRNA products are also commercially available, and may be suitably employed in the method of the invention. See, e.g., Dharmacon, Inc., Lafayette, Colo. (Cat Nos. M-003162-03, MU-003162-03, D-003162-07 thru -10 (siGENOME™ SMARTselection and SMARTpool® siRNAs).

It has recently been established that small dsRNA less than 49 nucleotides in length, and preferably 19-25 nucleotides, comprising at least one sequence that is substantially identical to part of a target mRNA sequence, and which dsRNA optimally has at least one overhang of 1-4 nucleotides at an end, are most effective in mediating RNAi in mammals. See U.S. Patent Publication Nos. 20040038921 and 20040229266. The construction of such dsRNA, and their use in pharmaceutical preparations to silence expression of a target protein, in vivo, are described in detail in such publications.

If the sequence of the gene to be targeted in a mammal is known, 21-23 nt RNAs, for example, can be produced and tested for their ability to mediate RNAi in a mammalian cell, such as a human or other primate cell. Those 21-23 nt RNA molecules shown to mediate RNAi can be tested, if desired, in an appropriate animal model to further assess their in vivo effectiveness. Target sites that are known, for example target sites determined to be effective target sites based on studies with other nucleic acid molecules, for example ribozymes or antisense, or those targets known to be associated with a disease or condition such as those sites containing mutations or deletions, can be used to design siRNA molecules targeting those sites as well.

Alternatively, the sequences of effective dsRNA can be rationally designed/predicted screening the target mRNA of interest for target sites, for example by using a computer folding algorithm. The target sequence can be parsed in silico into a list of all fragments or subsequences of a particular length, for example 23 nucleotide fragments, using a custom Perl script or commercial sequence analysis programs such as Oligo, MacVector, or the GCG Wisconsin Package.

Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using in vitro RNA cleavage assays, cell culture, or animal models. See, e.g., U.S. Patent Publication No. 20030170891. An algorithm for identifying and selecting RNAi target sites has also recently been described. See U.S. Patent Publication No. 20040236517.

Commonly used gene transfer techniques include calcium phosphate, DEAE-dextran, electroporation and microinjection and viral methods (Graham et al. (1973) *Virol.* 52: 456; McCutchan et al., (1968), *J. Natl. Cancer Inst.* 41: 351; Chu et al. (1987), *Nucl. Acids Res.* 15: 1311; Fraley et al. (1980), *J. Biol. Chem.* 255: 10431; Capecchi (1980), *Cell* 22: 479). DNA may also be introduced into cells using cationic liposomes (Feigner et al. (1987), *Proc. Natl. Acad. Sci USA* 84: 7413). Commercially available cationic lipid formulations include Tfx 50 (Promega) or Lipofectamin 200 (Life Technologies). Alternatively, viral vectors may be employed to deliver dsRNA to a cell and mediate RNAi. See U.S. Patent Publication No. 20040023390.

Transfection and vector/expression systems for RNAi in mammalian cells are commercially available and have been well described. See, e.g., Dharmacon, Inc., DharmaFECT™ system; Promega, Inc., siSTRIKE™ U6 Hairpin system; see also Gou et al. (2003) *FEBS.* 548, 113-118; Sui, G. et al. A DNA vector-based RNAi technology to suppress gene expression in mammalian cells (2002) *Proc. Natl. Acad. Sci.* 99, 5515-5520; Yu et al. (2002) *Proc. Natl. Acad. Sci.* 99, 6047-6052; Paul, C. et al. (2002) *Nature Biotechnology* 19, 505-508; McManus et al. (2002) *RNA* 8, 842-850.

siRNA interference in a mammal using prepared dsRNA molecules may then be effected by administering a pharmaceutical preparation comprising the dsRNA to the mammal. The pharmaceutical composition is administered in a dosage sufficient to inhibit expression of the target gene. dsRNA can typically be administered at a dosage of less than 5 mg dsRNA per kilogram body weight per day, and is sufficient to inhibit or completely suppress expression of the target gene. In general a suitable dose of dsRNA will be in the range of 0.01 to 2.5 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. A pharmaceutical composition comprising the dsRNA is administered once daily, or in multiple sub-doses, for example, using sustained release formulations well known in the art. The preparation and administration of such pharmaceutical compositions may be carried out accordingly to standard techniques, as further described below.

Such dsRNA may then be used to inhibit ALK expression and activity in a cancer, by preparing a pharmaceutical preparation comprising a therapeutically-effective amount of such dsRNA, as described above, and administering the preparation to a human subject having a cancer (e.g., kidney cancer) expressing an ALK fusion protein or aberrantly expressing full length ALK polypeptide, for example, via direct injection to the tumor. The similar inhibition of other receptor tyrosine kinases, such as VEGFR and EGFR using siRNA inhibitors has been described. See U.S. Patent Publication No. 20040209832, U.S. Patent Publication No. 20030170891, and U.S. Patent Publication No. 20040175703.

ALK inhibitors (or their pharmaceutically acceptable salts) are to be provided to patients in an amount/dosage, frequency and form (including standard excipients if needed) as determined by a competent clinician or pharmacist. The inhibitors may be provided orally, parentally, intravenously, for example. If the PF02341066 is used as an ALK inhibitor in the context of the invention, guidance for its delivery, dosage and formulation may be found in U.S. Pub. No. 2008/0300273, for example.

Of course ALK-inhibiting therapeutic compositions useful in the practice of the methods of the invention may be administered to a mammal by any means known in the art including, but not limited to oral or peritoneal routes, including intravenous, intramuscular, intraperitoneal, subcutaneous, transdermal, airway (aerosol), rectal, vaginal and topical (including buccal and sublingual) administration.

For oral administration, a ALK-inhibiting therapeutic will generally be provided in the form of tablets or capsules, as a powder or granules, or as an aqueous solution or suspension. Tablets for oral use may include the active ingredients mixed with pharmaceutically acceptable carriers and excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. The carrier may consist exclusively of an aqueous buffer ("exclusively" means no auxiliary agents or encapsulating substances are present which might affect or mediate uptake of the ALK-inhibiting therapeutic). Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

ALK-inhibiting therapeutic compositions may also include encapsulated formulations to protect the therapeutic (e.g., a dsRNA compound or an antibody that specifically binds an ALK fusion polypeptide) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075. An encapsulated formulation may comprise a viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

ALK-inhibiting compounds can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.*, 2, 139; DELIVERY STRATEGIES FOR ANTISENSE OLIGONUCLEOTIDE THERAPEUTICS, ed. Akbtar, 1995, Maurer et al., 1999, *Mol. Membr. Biol.*, 16, 129-140; Hofland and Huang, 1999, *Handb. Exp. Pharmacol.*, 137, 165-192; and Lee et al., 2000, ACS Symp. Ser., 752, 184-192. U.S. Pat. No. 6,395,713 and PCT Publication No. WO 94/02595 further describe the general methods for delivery of nucleic acid molecules. These protocols can be utilized for the delivery of virtually any nucleic acid molecule.

ALK-inhibiting therapeutics can be administered to a mammalian tumor by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (see PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, *Clin. Cancer Res.*, 5, 2330-2337 and PCT Publication No. WO 99/31262.

Pharmaceutically acceptable formulations of ALK-inhibiting therapeutics include salts of the above described compounds, e.g., acid addition salts, for example, salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

Administration routes that lead to systemic absorption (e.g., systemic absorption or accumulation of drugs in the blood stream followed by distribution throughout the entire body), are desirable and include, without limitation: intravenous, subcutaneous, intraperitoneal, inhalation, oral, intrapulmonary and intramuscular. Each of these administration routes exposes the ALK-inhibiting therapeutic to an accessible diseased tissue or tumor. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, *Fundam. Clin. Pharmacol.*, 13, 16-26); biodegradable polymers, such as poly (DL-lactide-coglycolide) microspheres for sustained release delivery after intracerebral implantation (Emerich et al, 1999, *Cell Transplant*, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (*Prog Neuro-psychopharmacol Biol Psychiatry*, 23, 941-949, 1999). Other non-limiting examples of delivery strategies for the ALK-inhibiting compounds useful in the method of the invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

Therapeutic compositions comprising surface-modified liposomes containing poly (ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta*, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; PCT Publication No. WO 96/10391; PCT Publication No. WO 96/10390; and PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Therapeutic compositions may include a pharmaceutically effective amount of the desired compounds in a pharmaceutically acceptable carrier or diluent. Acceptable carriers or diluents for therapeutic use are well known in the pharmaceutical art, and are described, for example, in REMINGTON'S PHARMACEUTICAL SCIENCES, Mack Publishing Co. (A. R. Gennaro edit. 1985). For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

An ALK-inhibiting therapeutic useful in the practice of the invention may comprise a single compound as described above, or a combination of multiple compounds, whether in the same class of inhibitor (e.g., antibody inhibitor), or in different classes (e.g., antibody inhibitors and small-molecule inhibitors). Such combination of compounds may increase the overall therapeutic effect in inhibiting the progression of a fusion protein-expressing cancer. For example, Crizotinib (also known as PF-02341066) produced by Pfizer, Inc. (see U.S. Pub. No. 2008/0300273) may be administered alone, or in combination with other Crizotinib analogues targeting ALK activity and/or small molecule inhibitors of ALK, such as NVP-TAE684 produced by Novartis, Inc. The therapeutic composition may also comprise one or more non-specific chemotherapeutic agent in addition to one or more targeted inhibitors. Such combinations have recently been shown to provide a synergistic tumor killing effect in many cancers. The effectiveness of such combinations in inhibiting ALK activity and tumor growth in vivo can be assessed according to standard methods.

The present invention is further directed to a method of monitoring the effectiveness of a cancer therapy, such as kidney cancer therapy. The method involves detecting the expression levels or activity levels of a polypeptide with ALK kinase activity in the relevant biological sample of the cancer patient prior to and after the cancer therapy. The expression levels of the polypeptide with ALK kinase activity are further quantified so as to be able to compare the values prior to therapy and after therapy. An increase or steady value in the expression and/or levels of the polypeptide with ALK kinase activity after therapy as compared to before therapy indicates that the cancer therapy is not effective. A decrease in the expression and/or activity level of the polypeptide with ALK kinase activity (i.e., the level of the polypeptide with ALK kinase activity is less after the therapy compared to prior to therapy) indicates an effective cancer therapy. In accordance with the invention, the cancer therapy may include biological therapies, such as surgery, immunotherapeutics, chemotherapeutics, and radiation therapies, and targeted therapies, such as drugs or other substances intended to block the growth and spread of cancer by interfering with specific molecular in tumor growth. ALK inhibitor treatments, such as the use of crizotinib (PF02341066), may be monitored according to the present invention.

The invention further provides a method for determining whether a compound inhibits the progression of a cancer (e.g., a kidney cancer) driven by polypeptide with ALK kinase activity. In this embodiment, the method comprises the step of determining whether the compound inhibits the expression and/or activity of the polypeptide with ALK kinase activity in the cancer. In some embodiments, inhibition of expression and/or activity of the polypeptide with ALK kinase is determined by examining a biological sample comprising cells from bone marrow, blood, or a tumor. In another embodiment, inhibition of expression and/or activity of polypeptide with ALK kinase is determined using at least one detection molecule as described herein.

The tested compound may be any type of therapeutic or composition as described above. Methods for assessing the efficacy of a compound, both in vitro and in vivo, are well established and known in the art. For example, a composition may be tested for ability to inhibit ALK in vitro using a cell or cell extract in which ALK kinase is activated. A panel of compounds may be employed to test the specificity of the compound for ALK (as opposed to other targets, such as EGFR or PDGFR).

Another technique for drug screening which may be used provides for high throughput screening of compounds having suitable binding affinity to a protein of interest, as described in PCT Publication No. WO 84/03564. In this method, as applied to ALK fusion polypeptides or full-length ALK polypeptide, large numbers of different small test compounds are synthesized on a solid substrate, such as plastic pins or some other surface. The test compounds are reacted with a polypeptide of the invention, or fragments thereof, and washed. Bound polypeptide is then detected by methods well known in the art. A purified polypeptide can also be coated directly onto plates for use in the aforementioned drug screening techniques. Alternatively, non-neutralizing antibodies can be used to capture the peptide and immobilize it on a solid support.

A compound found to be an effective inhibitor of ALK activity in vitro may then be examined for its ability to inhibit the progression of a cancer expressing a polypeptide with kinase activity (such as kidney cancer), in vivo, using, for example, mammalian xenografts harboring human kidney tumors that are express a polypeptide with ALK kinase activity. In this procedure, cancer cell lines known to express a polypeptide with ALK kinase activity may be placed subcutaneously in an animal (e.g., into a nude or SCID mouse, or other immune-compromised animal). The cells then grow into a tumor mass that may be visually monitored. The animal may then be treated with the drug. The effect of the drug treatment on tumor size may be externally observed. The animal is then sacrificed and the tumor removed for analysis by IHC and Western blot. Similarly, mammalian bone marrow transplants may be prepared, by standard methods, to examine drug response in hematological tumors expressing a mutant ALK kinase. In this way, the effects of the drug may be observed in a biological setting most closely resembling a patient. The drug's ability to alter signaling in the tumor cells or surrounding stromal cells may be determined by analysis with phosphorylation-specific antibodies. The drug's effectiveness in inducing cell death or inhibition of cell proliferation may also be observed by analysis with apoptosis specific markers such as cleaved caspase 3 and cleaved PARP.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the compounds exhibit high therapeutic indices.

The following Examples are provided only to further illustrate the invention, and are not intended to limit its scope, except as provided in the claims appended hereto. The present invention encompasses modifications and variations of the methods taught herein which would be obvious to one of ordinary skill in the art. Materials, reagents and the like to which reference is made are obtainable from commercial sources, unless otherwise noted.

Example 1

Identification of ALK or ALK Fusion Polypeptides in Kidney Cancer Patients

Tissue microarrays comprised of samples of cancers of the breast, pancreas, prostate, bladder, endometrium, kidney and various metastases were obtained from BioChain Institute, Inc., Hayward, Calif.

Tissue arrays were deparaffinized through three changes of xylene for 5 minutes each, then rehydrated through two changes of 100% ethanol and 2 changes of 95% ethanol, each for 5 minutes. Slides were rinsed for 5 minutes each in three changes of diH$_2$O, then were subjected to antigen retrieval in a Decloaking Chamber (Biocare Medical, Concord, Calif.) as follows. Slides were immersed in 250 ml 1.0 mM EDTA, pH 8.0 in a 24 slide holder from Tissue Tek. The Decloaking Chamber was filled with 500 ml diH2O, the slide holder was placed in the chamber touching the heat shield, and retrieval was performed with the following settings as set by the manufacturer: SP1 125° C. for 30 seconds and SP2 90° C. for 10 seconds. Slides were cooled on the bench for 10 minutes, rinsed in diH$_2$O, submerged in 3% H$_2$O$_2$ for 10 minutes, then washed twice in diH$_2$O. After blocking for 1 hour at room temperature in Tris buffered saline+0.5% Tween-20 (TBST)/5% goat serum in a humidified chamber, slides were incubated overnight at 4° C. with ALK (D5F3) XP® Rabbit mAb (Cell Signaling Technology, Inc., Danvers, Mass.; Catalog No. 3633) at 9.8 µg/ml diluted in SignalStain® Antibody Diluent (Catalog No. 8112 Cell Signaling Technology, Inc.). After washing three times in TBST, detection was performed with Envision+ (DAKO, Carpinteria, Calif.) with a 30 minute incubation at room temperature in a humidified chamber. After washing three times in TBST slides were exposed to NovaRed (Vector Laboratories, Burlingame, Calif.) prepared per the manufacturer's instructions. Slides were developed for 1 minute then rinsed in diH$_2$O. Slides were counterstained by incubating in hematoxylin (Ready to Use Invitrogen, Carlsbad, Calif.; Catalog #00-8011) for 1 minute, rinsed for 30 seconds in diH2O, incubated for 20 seconds in bluing reagent (Richard Allan Scientific, Catalog #7301), then finally washed for 30 seconds in diH2O. Slides were dehydrated in 2 changes of 95% ethanol for 20 seconds each and 2 changes of 100% ethanol for 2 minutes each. Slides were cleared in 2 changes of xylene for 20 seconds each, then air dried. Coverslips were mounted using VectaMount (Vector Laboratories, Burlingame, Calif.). Slides were air dried, then evaluated under the microscope.

Staining was observed in 1 lymphoma in the kidney and 1 squamous cell carcinoma of the kidney.

Figure 2:
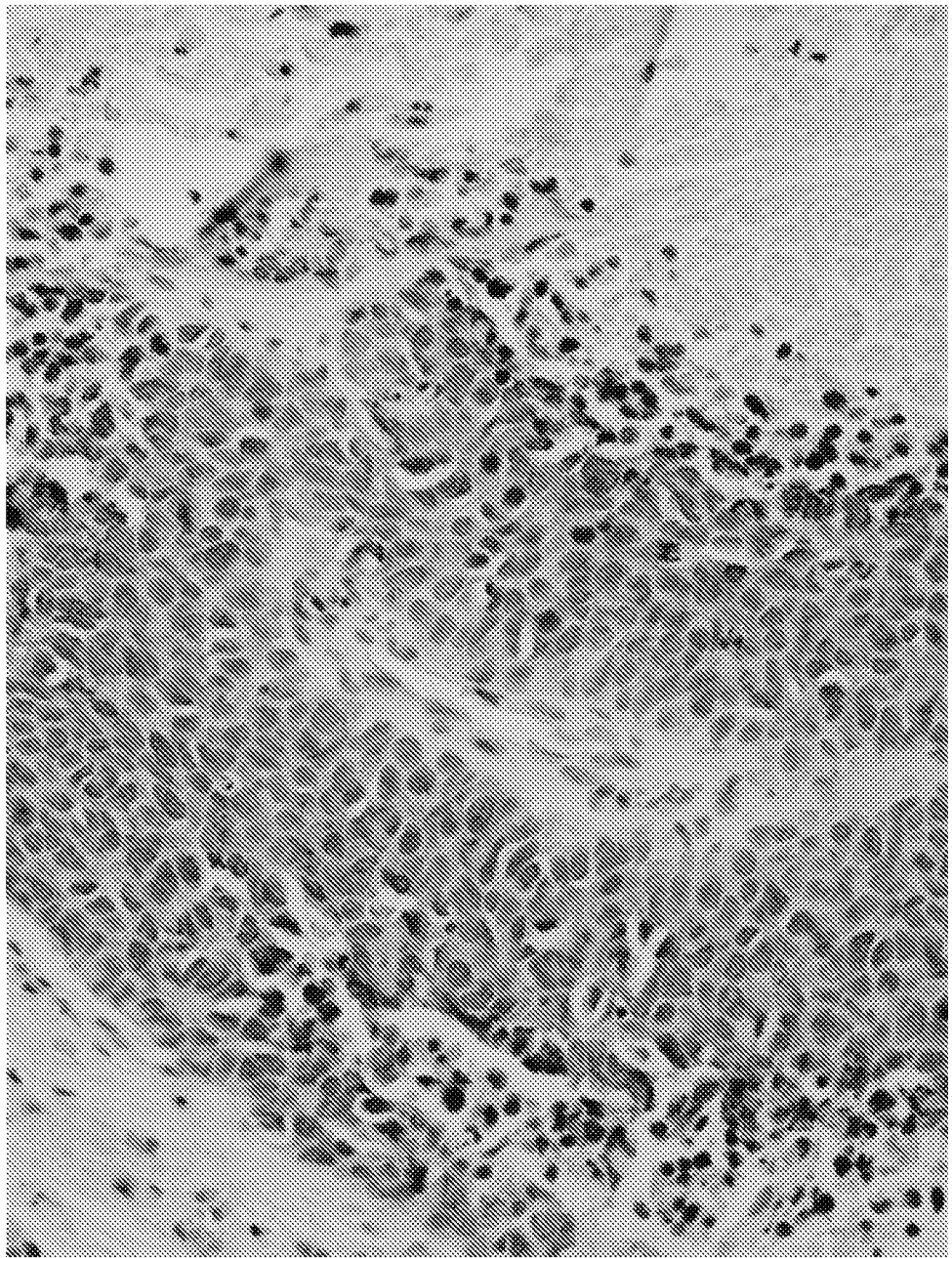
FIG. 2 is an immunohistochemical representation demonstrating ALK-specific monoclonal antibody staining of granular cell carcinoma of the kidney.

Additional arrays of kidney carcinomas and normal kidney tissue (331 carcinomas and 26 normal tissues) were acquired from BioChain Institute, Inc., Hayward, Calif. and Folio Biosciences Columbus, Ohio and stained with ALK (D5F3) XP® Rabbit mAb as described above. Staining was observed in 1 squamous cell carcinoma of the kidney (FIG. 1) and 1 granular cell carcinoma (FIG. 2).

Total kidney cancer cases stained, including lymphomas: 331
Positive cases identified: 4
Frequency: 1.2%
Total cancers stained, excluding lymphoma: 327
Positive cases identified: 3
Frequency: 0.9%
Breakdown of frequency by cancer type:

TABLE 1

| Cancer | Cases | Positive Staining | Frequency |
| --- | --- | --- | --- |
| Granular cell | 26 | 1 | 3.8% |
| Squamous cell | 9 | 2 | 22.2% |
| Lymphoma | 4 | 1 | 25% |

Example 2

Evaluation of ALK in Kidney Using FISH Analysis

Figure 3:
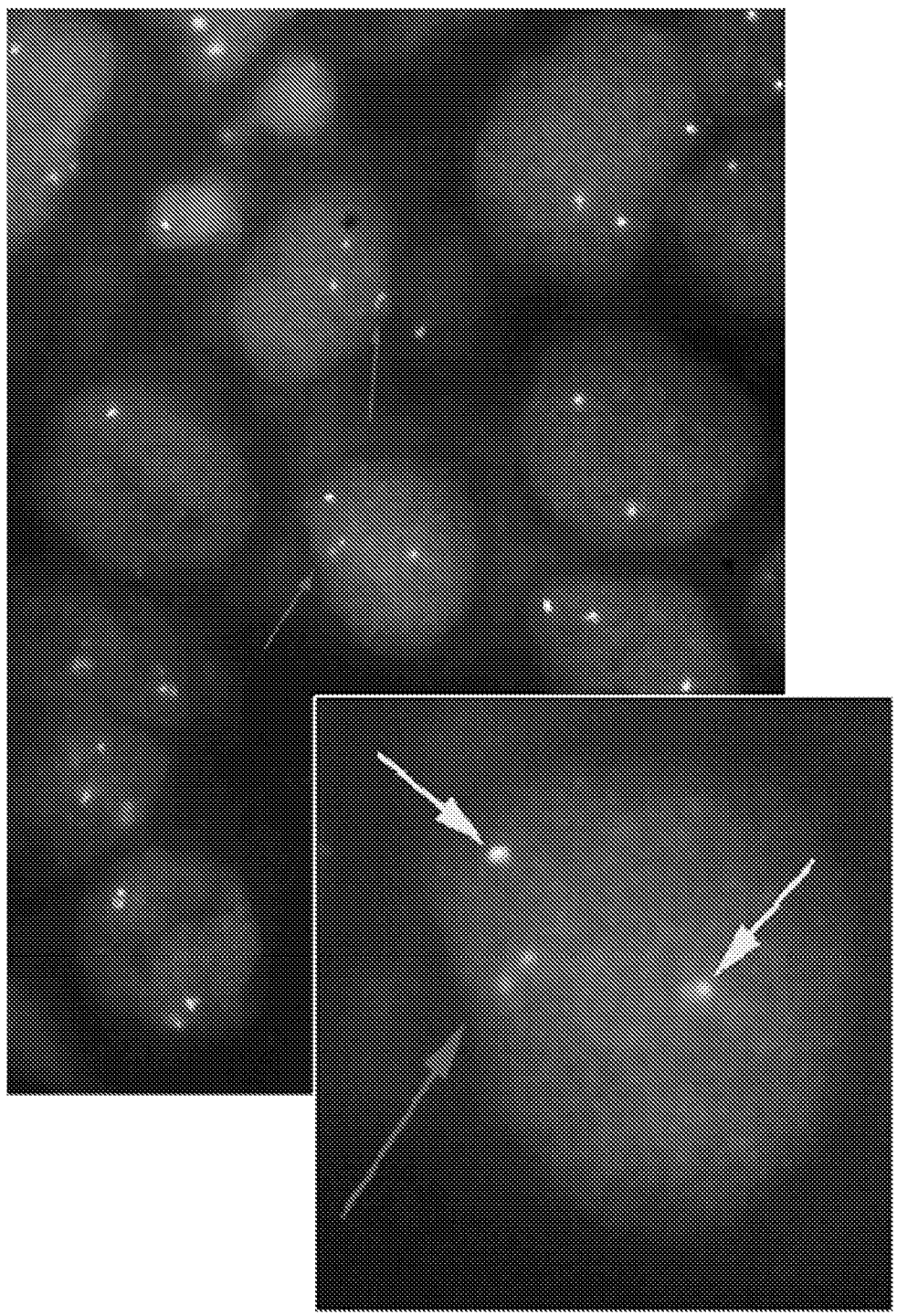
FIG. 3 is an image (with the inset showing a expanded view of the cell immediately to the upper right of the inset) depicting the detection of ALK by FISH assay employing a dual-color (orange/green) break-apart probe specific to the ALK locus in kidney squamous cells. The yellow arrows point to orange/green signals either immediately adjacent to each other or fused together confirming the presence of the 2p23 ALK region in its native state. The red arrows point to a rearranged ALK locus. Images were taken at 100× magnification with digital zoom inset.

ALK was analyzed by fluorescent in situ hybridization (FISH) in a lymphoma tissue of the kidney (Z7020052 I6/J6) and a squamous cell carcinoma tissue of the kidney (Z6020052 G8/H8) with the use of a break-apart probe specific to the ALK locus (Vysis LSI ALK Dual Color, Break Apart Rearrangement Probe; Abbott Molecular). The Vysis probe contains two differently labeled probes on opposite sides of the breakpoint of the ALK gene: one approximately 250 kb probe for the telomeric side of the ALK breakpoint is labeled with SpectrumOrange and the centromeric probe is approximately 300 kb and labeled with SpectrumGreen. When hybridized with the LSI ALK Dual Color, Break Apart Rearrangement Probe, the 2p23 ALK region in its native state is seen as two immediately adjacent or fused orange/green (yellow) signals. Paraffin embedded tissue sections were re-hydrated and incubated for 1 hour in TE buffer pH 8 in boiling water. Sections were digested with pepsin Digest All III (Invitrogen) at 37° C. for 20-40 minutes. Slides were then fixed with NBF for 1 minute and then dehydrated. The probe and tissue were then co-denatured at 93° C. for 3 minutes and then allowed to incubate at 37° C. for 18 hours. After washing, 4',6-diamidino-2-phenylindole (DAPI; mg/ml) in Vectashield mounting medium (Vector Laboratories, Burlingame, Calif.) was applied for nuclear counterstaining Cytogenetic rearrangement of the ALK locus were confirmed by FISH in the kidney lymphoma and squamous cell carcinoma of the kidney (FIG. 3). The results (with IHC results of the same tissues) are summarized in Table 2.

TABLE 2

| TUMOR ID | TYPE | ALK IHC | ALK FISH |
|---|---|---|---|
| Z7020052 I6/J6 | Kidney Lymphoma | + | + |
| Z6020052 G8/H8 | Kidney Squamous | + | + |

Example 3

Evaluation of MDCK for ALK and c-Met in Western Blot Experiment

U.S. Patent Application Publication No. 2008/0300273, herein incorporated by reference, describes the application of the c-Met and ALK inhibitor, crizotinib (PF-02341066) to Madin-Darby Canine Kidney (MDCK) cell lines to reduce HGF-stimulated cell scattering.

HGF-stimulated MDCK cell lines were evaluated to assess whether crizotinib was acting by inhibition of c-Met or ALK using antibodies specific for either c-Met, ALK or ALK fusion polypeptides.

MDCK were maintained in Dulbecco's modified Eagle's medium supplemented with 10% fetal bovine serum. The cells were serum-starved overnight and then either stimulated with hepatocyte growth factor (HGF) (50 ng/ml) at 37° C. for 5 min or 24 h, or serum-starved for an additional 5 min or 24 h. Cells were then washed in ice-cold PBS, treated with 1× Cell Lysis Buffer (20 mM Tris-HCl (pH7.5), 150 mM NaCl, 1 mM Na$_2$EDTA, 1 mM EGTA, 1% Triton, 2.5 mM sodium pyrophosphate, 1 mM beta-glycerophosphate, 1 mM Na$_3$VO$_4$, 1 ug/mL leupeptin, 1% SDS and 40 mM DTT) for 5 min on ice, and then scraped. H3122 cells (expressing EML4-ALK fusion polypeptide) were used as a positive control for ALK. MKN45 cells were used as a positive control for pMet.

The MDCK, H3122, and MKN45 cell lysates were analyzed by Western Blot. The membranes were probed with the following antibodies: pMet Y1234/5 antibody (Cell Signaling Technology, #3077), Met (25H2) mouse monoclonal antibody (Cell Signaling Technology, #3127), pALK Y1278/82/83 antibody (Cell Signaling Technology #3983), ALK (D5F3) XP®RmAb (Cell Signaling Technology #3633), and Beta Actin (Cell Signaling Technology #4970).

The results of the Western blot are represented by a 1 second exposure (FIG. 4A) and a 15 second exposure (FIG. 4B). As shown, the MDCK cells (lanes 1, 2, 3, and 4) are positive for Met (Cell Signaling Technology #3127), but not ALK (Cell Signaling Technology #3633).

These results demonstrate that MDCK cells stimulated by HGF do not express ALK. Therefore, to the extent crizotinib inhibits MDCK cell scattering in response to HGF stimulation, the mechanism of action appears to be that it inhibits c-Met/HGFR activity.

Therefore, inhibition of MDCK cell lines in scattering assays, as described in the US Patent Publication 2008/0300273, appears to be acting through Met-related activity and not ALK activity.

Example 4

Detection of ALK or ALK Fusion Polypeptide Expression in a Human Cancer Sample Using PCR Assay The presence of ALK and/or an ALK fusion polypeptide of the invention in cancer sample is detected using RT-PCR. These methods have been previously described. See, e.g., Cools et al., N. Engl. J. Med. 348: 1201-1214 (2003).

PCR Assay

To confirm the existence of an EML4-ALK fusion gene in genomic DNA, standard PCR methods known in the art for detecting the relevant translocation may be used.

Genomic PCR is done with 50 to 100 ng of DNA in a 25 µL reaction containing LongAmp Taq DNA polymerase (New England Biolabs, Ipswich, Mass.) under the following conditions: 3 min at 95° C. followed by 30 cycles of 10 s at 95° C., 1 min at 55° C., and 10 min at 68° C. plus a final extension for 20 min at 68° C. The genomic fusion points for the E13; A20 variant are identified using forward PCR primer Fusion-genome-S or a primer residing in EML4 intron 13 (AGGA GAGAAAGAGCTGCAGTG) (SEQ ID NO: 7) and reverse primer Fusion-genome-AS or a primer located in ALK intron 19 (GCTCTGAACCTTTCCATCAT-ACTT) (SEQ ID NO:8). For the detection of the E20; A20 and E21; A20 variants, the forward primers are placed within EML4 exon 20 (ACTGGTCCCCAGACAACAAG) (SEQ ID NO:9) or intron 20 (TTACTCTGTCAAATTGAT-GCTGCT) (SEQ ID NO:10), whereas the reverse primer is Fusion-genome-AS. The PCR products are resolved on agarose gel; if they appear specific, the original PCR product is used for direct sequencing. However, if additional non-specific fragments are present, the desired fragments are excised, gel purified, cloned, and sequenced.

A fusion partner of ALK is determined by performing RNA ligase-mediated rapid amplification of 5' and 3' cDNA ends with GeneRacer kit (Invitrogen). First-strand cDNA is amplified with Advantage HD DNA polymerase mix (Clontech) using GeneRacer 5' primer and ALK-6R primer (CAT-GAGGAAATCCAGTTCGTCCTG) (SEQ ID NO:11). Subsequent nested PCR is done using GeneRacer 5' nested primer and ALK-2R primer (GAGGTCTTGCCAG-CAAAGCAGTAG) (SEQ ID NO:12). Amplification products are gel purified with QIAquick gel extraction (Qiagen) and cloned using pCR4-TOPO TA Cloning (Invitrogen). Sequencing is done using 3730×1 DNA Analyzer (Applied Biosystems). Sequencing products may be analyzed with Sequencer software (Gene Codes). Basic Local Alignment and Search Tool against the BLAT database4 is used to determine the identity of unknown sequences To determine whether EML4-ALK gene product is expressed, RT-PCR is performed on RNA extracted from the kidney cancer cell samples of patients. RT-PCR is carried out using One Step RT-PCR (Qiagen) and primers previously described in (Soda et al., Nature 2007; 448:561-6. Choi Y L, Takeuchi K, Soda M, et al. Identification of novel isoforms of the EML4-ALK transforming gene in non-small cell lung cancer. Cancer Res 2008; 68:4971-76. PCR conditions for the detection of EML4-ALK fusion transcript include cDNA synthesis at 50° C. for 30 min, denaturation at 95° C. for 15 min, 40 cycles consisting of denaturation at 95° C. for 30 s, annealing at 60° C. for 30 s, and strand elongation at 72° C. for 1 min and a final elongation step at 72° C. for 10 min. As an internal control, primers for the glyceraldehyde-3-phosphate dehydrogenase (GAPDH; AACGACCACTTTGTCAAGCTC (SEQ ID NO:13) and CTCTCTTCCTCTTGTGCTCTTGC) (SEQ ID NO:14) are used. Twenty cycles of amplification are performed. PCR products are resolved on agarose gel and their sizes are determined by using Trackit 1 kb Plus DNA ladder (Invitrogen). Fragments representing EML4-ALK fusion product are excised, gel purified, cloned, and sequenced.

Expression of ALK Protein or ALK Fusion Polypeptide

The expression of ALK and ALK fusion polypeptides is investigated by Western blotting and immunoprecipitation with anti-ALK antibodies.

Cell lysates are prepared from kidney cancer cells by removing media and rinsing the cells with ice-cold PBS. The PBS is removed and 0.5 ml ice-cold 1× cell lysis buffer (20 mM Tris pH 7.5, 150 mM NaCl, 1 mM EDTA, 1 mM EGTA, 1% Triton X-100, 2.5 mM Sodium pyrophosphate, 1 mM β-glycerophosphate, 1 mM $Na_3VO_4$, 1 µg/ml Leupeptin) is added to each plate and incubated. The cells are transferred to micro centrifuge tubes and samples are sonicated on ice three times for 5 second each and microcentrifuged for 10 min at 14,000×g.

The cell lysate is incubated with the primary antibodies specific for ALK protein, pALK Y1278/82/83 antibody (CST #3893) and ALK (D5F3) XP™ RmAb (CST #3633) overnight at 4° C. Protein A or G agarose beads are added and incubated with gentle rocking for 1-3 hours at 4° C. The sample is microcentrifuged for 30 s at 4° C., washed, and resuspended with 20 µl 3×SDS sample buffer. The sample is loaded on an SDS-PAGE gel and analyzed by Western blotting.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method, comprising
   contacting a biological sample from a human kidney cancer or suspected kidney cancer, with a detectably labeled antibody that specifically binds to a fragment of a wild type Anaplastic Lymphoma Kinase (ALK), wherein the fragment is the ALK kinase domain as set forth in SEQ ID NO: 3 or the intracytoplasmic domain of ALK as set forth in SEQ ID NO: 4,
   detecting the presence of a polypeptide comprising the ALK fragment based on detecting the binding of said antibody to the ALK fragment, and
   performing an assay to determine that the polypeptide is an EML4-ALK fusion protein.

2. The method of claim 1, wherein said kidney cancer is a granular cell cancer or a squamous cell cancer.

3. The method of claim 1, wherein said biological sample comprises at least one circulating tumor cell from said kidney cancer.

4. The method of claim 1, wherein said biological sample comprises cells obtained from a tumor biopsy, a tumor fine needle aspirate, or a pleural effusion.

5. The method of claim 1, wherein the sample is a kidney tissue sample containing tumor cells and is prepared for immunochemical staining.

* * * * *

SEQUENCE LISTING

```
<160> NUMBER OF SEQ ID NOS: 15

<210> SEQ ID NO 1
<211> LENGTH: 6226
<212> TYPE: DNA
<213> ORGANISM: Artificial Sequence
<220> FEATURE:
<223> OTHER INFORMATION: Synthetic Polynucleotide

<400> SEQUENCE: 1 aagcggggc  ggcagcggtg  gtagcagctg  gtacctcccg  ccgcctctgt  tcggagggtc      60
gcggggcacc  gaggtgcttt  ccggccgccc  tctggtcggc  cacccaaagc  cgcgggcgct     120
gatgatgggt  gaggaggggg  cggcaagatt  tcgggcgccc  ctgccctgaa  cgccctcagc     180
tgctgccgcc  ggggccgctc  cagtgcctgc  gaactctgag  gagccgaggc  gccggtgaga     240
gcaaggacgc  tgcaaacttg  cgcagcgcgg  gggctgggat  tcacgcccag  aagttcagca     300
ggcagacagt  ccgaagcctt  cccgcagcgg  agagatagct  tgagggtgcg  caagacggca     360
gcctccgccc  tcggttcccg  cccagaccgg  gcagaagagc  ttggaggagc  cacaaggaac     420
gcaaaaggcg  gccaggacag  cgtgcagcag  ctggagccg   ccgttctcag  ccttaaaagt     480
tgcagagatt  ggaggctgcc  ccgagagggg  acagacccca  gctccgactg  cggggggcag     540
gagaggacgg  tacccaactg  ccacctccct  tcaaccatag  tagttcctct  gtaccgagcg     600
cagcgagcta  cagacggggg  cgcggcactc  ggcgcggaga  gcgggaggct  caaggtccca     660
gccagtgagc  ccagtgtgct  tgagtgtctc  tggactcgcc  cctgagcttc  caggtctgtt     720
tcatttagac  tcctgctcgc  ctccgtgcag  ttgggggaaa  gcaagagact  tgcgcgcacg     780
cacagtcctc  tggagatcag  gtggaaggag  ccgctgggta  ccaaggactg  ttcagagcct     840
cttcccatct  cggggagagc  gaagggtgag  gctgggcccg  gagagcagtg  taaacggcct     900
cctccggcgg  gatgggagcc  atcgggctcc  tgtggctgct  gccgctgctg  ctttccacgg     960
cagctgtggg  ctccgggatg  gggaccggcc  agcgcgcggg  ctccccagct  gcggggtcgc    1020
cgctgcagcc  ccggagccca  ctcagctact  cgcgcctgca  gaggaagagt  ctggcagttg    1080
acttcgtggt  gccctcgctc  ttccgtgtct  acgcccggga  cctactgctg  ccaccatcct    1140
cctcggagct  gaaggctggc  aggcccgagg  cccgcggctc  gctagctctg  gactgcgccc    1200
cgctgctcag  gttgctgggg  ccggcgccgg  gggtctcctg  gaccgccggt  tcaccagccc    1260
```

-continued

```
cggcagaggc ccggacgctg tccagggtgc tgaagggcgg ctccgtgcgc aagctccggc    1320
gtgccaagca gttggtgctg gagctgggcg aggaggcgat cttggagggt tgcgtcgggc    1380
ccccgggga ggcggctgtg gggctgctcc agttcaatct cagcgagctg ttcagttggt    1440
ggattcgcca aggcgaaggg cgactgagga tccgcctgat gcccgagaag aaggcgtcgg    1500
aagtgggcag agagggaagg ctgtccgcgg caattcgcgc ctcccagccc cgccttctct    1560
tccagatctt cgggactggt catagctcct tggaatcacc aacaaacatg ccatctcctt    1620
ctcctgatta ttttacatgg aatctcacct ggataatgaa agactccttc cctttcctgt    1680
ctcatcgcag ccgatatggt ctggagtgca gctttgactt cccctgtgag ctggagtatt    1740
cccctccact gcatgacctc aggaaccaga gctggtcctg gcgccgcatc ccctccgagg    1800
aggcctccca gatggacttg ctggatgggc ctggggcaga gcgttctaag gagatgccca    1860
gaggctcctt tctccttctc aacacctcag ctgactccaa gcacaccatc ctgagtccgt    1920
ggatgaggag cagcagtgag cactgcacac tggccgtctc ggtgcacagg cacctgcagc    1980
cctctggaag gtacattgcc cagctgctgc cccacaacga ggctgcaaga gagatcctcc    2040
tgatgcccac tccagggaag catggttgga cagtgctcca gggaagaatc gggcgtccag    2100
acaacccatt tcgagtggcc ctggaataca tctccagtgg aaaccgcagc ttgtctgcag    2160
tggacttctt tgccctgaag aactgcagtg aaggaacatc cccaggctcc aagatggccc    2220
tgcagagctc cttcacttgt tggaatggga cagtcctcca gcttgggcag gcctgtgact    2280
tccaccagga ctgtgcccag ggagaagatg agagccagat gtgccggaaa ctgcctgtgg    2340
gtttttactg caactttgaa gatggcttct gtggctggac ccaaggcaca ctgtcacccc    2400
acactcctca gtggcaggtc aggacccttaa aggatgcccg gttccaggac caccaagacc    2460
atgctctatt gctcagtacc actgatgtcc ccgcttctga aagtgctaca gtgaccagtg    2520
ctacgtttcc tgcaccgatc aagagctctc catgtgagct ccgaatgtcc tggctcattc    2580
gtggagtctt gaggggaaac gtgtccttgg tgctagtgga gaacaaaacc gggaaggagc    2640
aaggcaggat ggtctggcat gtcgccgcct atgaaggctt gagcctgtgg cagtggatgg    2700
tgttgcctct cctcgatgtg tctgacaggt tctggctgca gatggtcgca tggtggggac    2760
aaggatccag agccatcgtg gcttttgaca atatctccat cagcctggac tgctacctca    2820
ccattagcgg agaggacaag atcctgcaga atacagcacc caaatcaaga aacctgtttg    2880
agagaaaccc aaacaaggag ctgaaacccg gggaaaattc accaagacag accccccatct    2940
ttgaccctac agttcattgg ctgttcacca catgtgggc cagcgggccc catgccccca    3000
cccaggcaca gtgcaacaac gcctaccaga actccaacct gagcgtggag gtggggagcg    3060
agggccccct gaaaggcatc cagatctgga aggtgccagc caccgacacc tacagcatct    3120
cgggctacgg agctgctggc gggaaaggcg ggaagaacac catgatgcgg tcccacggcg    3180
tgtctgtgct gggcatcttc aacctggaga aggatgacat gctgtacatc ctggttgggc    3240
agcagggaga ggacgcctgc cccagtacaa accagttaat ccagaaagtc tgcattggag    3300
agaacaatgt gatagaagaa gaaatccgtg tgaacagaag cgtgcatgag tgggcaggag    3360
gcggaggagg aggggtgga gccacctacg tatttaagat gaaggatgga gtgccggtgc    3420
ccctgatcat tgcagccgga ggtggcggca gggcctacgg ggccaagaca gacacgttcc    3480
acccagagag actggagaat aactcctcgg ttctagggct aaacggcaat tccgagccgc    3540
caggtggtgg aggtggctgg aatgataaca cttccttgct ctgggccgga aaatctttgc    3600
```

```
aggagggtgc caccggagga cattcctgcc cccaggccat gaagaagtgg gggtgggaga   3660
caagaggggg tttcggaggg ggtggagggg ggtgctcctc aggtggagga ggcggaggat   3720
atataggcgg caatgcagcc tcaaacaatg accccgaaat ggatgtgggaa gatggggttt   3780 ccttcatcag tccactgggc atcctgtaca ccccagcttt aaaagtgatg gaaggccacg   3840
gggaagtgaa tattaagcat tatctaaact gcagtcactg tgaggtagac gaatgtcaca   3900
tggaccctga aagccacaag gtcatctgct tctgtgacca cgggacggtg ctggctgagg   3960
atggcgtctc ctgcattgtg tcacccaccc cggagccaca cctgccactc tcgctgatcc   4020
tctctgtggt gacctctgcc ctcgtggccg ccctggtcct ggctttctcc ggcatcatga   4080
ttgtgtaccg ccggaagcac caggagctgc aagccatgca gatggagctg cagagccctg   4140
agtacaagct gagcaagctc cgcacctcga ccatcatgac cgactacaac cccaactact   4200
gctttgctgg caagacctcc tccatcagtg acctgaagga ggtgccgcgg aaaaacatca   4260
ccctcattcg gggtctgggc catggcgcct ttggggaggt gtatgaaggc caggtgtccg   4320
gaatgcccaa cgacccaagc cccctgcaag tggctgtgaa gacgctgcct gaagtgtgct   4380
ctgaacagga cgaactggat ttcctcatgg aagccctgat catcagcaaa ttcaaccacc   4440
agaacattgt tcgctgcatt ggggtgagcc tgcaatccct gccccggttc atcctgctgg   4500
agctcatggc gggggggagac ctcaagtcct tcctccgaga ccccgccct cgcccgagcc   4560 agccctcctc cctggccatg ctggaccttc tgcacgtggc tcgggacatt gcctgtggct   4620
gtcagtattt ggaggaaaac cacttcatcc accgagacat tgctgccaga aactgcctct   4680
tgacctgtcc aggccctgga agagtggcca agattgaga cttcgggatg gcccgagaca   4740
tctacagggc gagctactat agaaagggag gctgtgccat gctgccagtt aagtggatgc   4800
ccccagaggc cttcatggaa ggaatattca cttctaaaac agacacatgg tcctttggag   4860
tgctgctatg ggaaatcttt tctcttggat atatgccata ccccagcaaa agcaaccagg   4920
aagttctgga gtttgtcacc agtggaggcc ggatggaccc acccaagaac tgccctgggc   4980
ctgtataccg gataatgact cagtgctggc aacatcagcc tgaagacagg cccaactttg   5040
ccatcatttt ggagaggatt gaatactgca cccaggaccc ggatgtaatc aacaccgctt   5100
tgccgataga atatggtcca cttgtggaag aggaagagaa agtgcctgtg aggcccaagg   5160
accctgaggg ggttcctcct ctcctggtct ctcaacaggc aaaacgggag gaggagcgca   5220
gcccagctgc cccaccacct ctgcctacca cctcctctgg caaggctgca agaaaccca   5280 cagctgcaga ggtctctgtt cgagtcccta gagggccggc cgtggaaggg ggacacgtga   5340
atatggcatt ctctcagtcc aaccctcctt cggagttgca caaggtccac ggatccagaa   5400
acaagcccac cagcttgtgg aacccaacgt acggctcctg gtttacagag aaacccacca   5460
aaaagaataa tcctatagca aagaaggagc cacacgacag gggtaacctg gggctggagg   5520
gaagctgtac tgtcccacct aacgttgcaa ctgggagact tccggggggcc tcactgctcc   5580 tagagccctc ttcgctgact gccaatatga aggaggtacc tctgttcagg ctacgtcact   5640
tcccttgtgg gaatgtcaat tacggctacc agcaacaggg cttgcccctta aagccgcta   5700 ctgcccctgg agctggtcat tacgaggata ccattctgaa aagcaagaat agcatgaacc   5760
agcctgggcc ctgagctcgg tcgcacactc acttctcttc cttgggatcc ctaagaccgt   5820
ggaggagaga gaggcaatgg ctccttcaca aaccagagac caaatgtcac gttttgtttt   5880
gtgccaacct attttgaagt accaccaaaa aagctgtatt ttgaaaatgc tttagaaagg   5940
ttttgagcat gggttcatcc tattctttcg aaagaagaaa atatcataaa aatgagtgat   6000
```

-continued

```
aaatacaagg cccagatgtg gttgcataag gtttttatgc atgtttgttg tatacttcct    6060
tatgcttctt ttaaattgtg tgtgctctgc ttcaatgtag tcagaattag ctgcttctat    6120
gtttcatagt tggggtcata gatgtttcct tgccttgttg atgtggacat gagccatttg    6180
aggggagagg gaacggaaat aaaggagtta tttgtaatga ctaaaa                   6226
```

<210> SEQ ID NO 2
<211> LENGTH: 1620
<212> TYPE: PRT
<213> ORGANISM: Artificial Sequence
<220> FEATURE:
<223> OTHER INFORMATION: Synthetic Peptide

<400> SEQUENCE: 2

```
Met Gly Ala Ile Gly Leu Leu Trp Leu Leu Pro Leu Leu Ser Thr
1               5                  10                  15

Ala Ala Val Gly Ser Gly Met Gly Thr Gly Gln Arg Ala Gly Ser Pro
            20                  25                  30

Ala Ala Gly Ser Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
    50                  55                  60

Arg Val Tyr Ala Arg Asp Leu Leu Leu Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320
```

-continued

Leu Leu Leu Asn Thr Ser Ala Asp Ser Lys His Thr Ile Leu Ser Pro
            325                 330                 335

Trp Met Arg Ser Ser Glu His Cys Thr Leu Ala Val Ser Val His
        340                 345                 350

Arg His Leu Gln Pro Ser Gly Arg Tyr Ile Ala Gln Leu Leu Pro His
            355                 360                 365

Asn Glu Ala Ala Arg Glu Ile Leu Leu Met Pro Thr Pro Gly Lys His
        370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
            405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
        450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
            485                 490                 495

His Thr Pro Gln Trp Gln Val Arg Thr Leu Lys Asp Ala Arg Phe Gln
        500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
            565                 570                 575

Gln Gly Arg Met Val Trp His Val Ala Ala Tyr Glu Gly Leu Ser Leu
        580                 585                 590

Trp Gln Trp Met Val Leu Pro Leu Leu Asp Val Ser Asp Arg Phe Trp
        595                 600                 605

Leu Gln Met Val Ala Trp Trp Gly Gln Gly Ser Arg Ala Ile Val Ala
        610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
            645                 650                 655

Glu Arg Asn Pro Asn Lys Glu Leu Lys Pro Gly Glu Asn Ser Pro Arg
        660                 665                 670

Gln Thr Pro Ile Phe Asp Pro Thr Val His Trp Leu Phe Thr Thr Cys
        675                 680                 685

Gly Ala Ser Gly Pro His Gly Pro Thr Gln Ala Gln Cys Asn Asn Ala
690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
            725                 730                 735

Ser Gly Tyr Gly Ala Ala Gly Gly Lys Gly Gly Lys Asn Thr Met Met

-continued

```
                740                 745                 750
Arg Ser His Gly Val Ser Val Leu Gly Ile Phe Asn Leu Glu Lys Asp
        755                 760                 765
Asp Met Leu Tyr Ile Leu Val Gly Gln Gln Gly Glu Asp Ala Cys Pro
        770                 775                 780
Ser Thr Asn Gln Leu Ile Gln Lys Val Cys Ile Gly Glu Asn Asn Val
785                 790                 795                 800
Ile Glu Glu Glu Ile Arg Val Asn Arg Ser Val His Glu Trp Ala Gly
                805                 810                 815
Gly Gly Gly Gly Gly Gly Ala Thr Tyr Val Phe Lys Met Lys Asp
                820                 825                 830
Gly Val Pro Val Pro Leu Ile Ile Ala Ala Gly Gly Gly Arg Ala
        835                 840                 845
Tyr Gly Ala Lys Thr Asp Thr Phe His Pro Glu Arg Leu Glu Asn Asn
        850                 855                 860
Ser Ser Val Leu Gly Leu Asn Gly Asn Ser Gly Ala Ala Gly Gly Gly
865                 870                 875                 880
Gly Gly Trp Asn Asp Asn Thr Ser Leu Leu Trp Ala Gly Lys Ser Leu
                885                 890                 895
Gln Glu Gly Ala Thr Gly Gly His Ser Cys Pro Gln Ala Met Lys Lys
                900                 905                 910
Trp Gly Trp Glu Thr Arg Gly Gly Phe Gly Gly Gly Gly Gly Cys
                915                 920                 925
Ser Ser Gly Gly Gly Gly Gly Tyr Ile Gly Gly Asn Ala Ala Ser
        930                 935                 940
Asn Asn Asp Pro Glu Met Asp Gly Glu Asp Gly Val Ser Phe Ile Ser
945                 950                 955                 960
Pro Leu Gly Ile Leu Tyr Thr Pro Ala Leu Lys Val Met Glu Gly His
                965                 970                 975
Gly Glu Val Asn Ile Lys His Tyr Leu Asn Cys Ser His Cys Glu Val
                980                 985                 990
Asp Glu Cys His Met Asp Pro Glu Ser His Lys Val Ile Cys Phe Cys
                995                 1000                1005
Asp His Gly Thr Val Leu Ala Glu Asp Gly Val Ser Cys Ile Val
        1010                1015                1020
Ser Pro Thr Pro Glu Pro His Leu Pro Leu Ser Leu Ile Leu Ser
        1025                1030                1035
Val Val Thr Ser Ala Leu Val Ala Ala Leu Val Leu Ala Phe Ser
        1040                1045                1050
Gly Ile Met Ile Val Tyr Arg Arg Lys His Gln Glu Leu Gln Ala
        1055                1060                1065
Met Gln Met Glu Leu Gln Ser Pro Glu Tyr Lys Leu Ser Lys Leu
        1070                1075                1080
Arg Thr Ser Thr Ile Met Thr Asp Tyr Asn Pro Asn Tyr Cys Phe
        1085                1090                1095
Ala Gly Lys Thr Ser Ser Ile Ser Asp Leu Lys Glu Val Pro Arg
        1100                1105                1110
Lys Asn Ile Thr Leu Ile Arg Gly Leu Gly His Gly Ala Phe Gly
        1115                1120                1125
Glu Val Tyr Glu Gly Gln Val Ser Gly Met Pro Asn Asp Pro Ser
        1130                1135                1140
Pro Leu Gln Val Ala Val Lys Thr Leu Pro Glu Val Cys Ser Glu
        1145                1150                1155
```

-continued

Gln Asp Glu Leu Asp Phe Leu Met Glu Ala Leu Ile Ile Ser Lys
1160              1165              1170

Phe Asn His Gln Asn Ile Val Arg Cys Ile Gly Val Ser Leu Gln
1175              1180              1185

Ser Leu Pro Arg Phe Ile Leu Leu Glu Leu Met Ala Gly Gly Asp
1190              1195              1200

Leu Lys Ser Phe Leu Arg Glu Thr Arg Pro Arg Pro Ser Gln Pro
1205              1210              1215

Ser Ser Leu Ala Met Leu Asp Leu Leu His Val Ala Arg Asp Ile
1220              1225              1230

Ala Cys Gly Cys Gln Tyr Leu Glu Glu Asn His Phe Ile His Arg
1235              1240              1245

Asp Ile Ala Ala Arg Asn Cys Leu Leu Thr Cys Pro Gly Pro Gly
1250              1255              1260

Arg Val Ala Lys Ile Gly Asp Phe Gly Met Ala Arg Asp Ile Tyr
1265              1270              1275

Arg Ala Ser Tyr Tyr Arg Lys Gly Gly Cys Ala Met Leu Pro Val
1280              1285              1290

Lys Trp Met Pro Pro Glu Ala Phe Met Glu Gly Ile Phe Thr Ser
1295              1300              1305

Lys Thr Asp Thr Trp Ser Phe Gly Val Leu Leu Trp Glu Ile Phe
1310              1315              1320

Ser Leu Gly Tyr Met Pro Tyr Pro Ser Lys Ser Asn Gln Glu Val
1325              1330              1335

Leu Glu Phe Val Thr Ser Gly Gly Arg Met Asp Pro Pro Lys Asn
1340              1345              1350

Cys Pro Gly Pro Val Tyr Arg Ile Met Thr Gln Cys Trp Gln His
1355              1360              1365

Gln Pro Glu Asp Arg Pro Asn Phe Ala Ile Ile Leu Glu Arg Ile
1370              1375              1380

Glu Tyr Cys Thr Gln Asp Pro Asp Val Ile Asn Thr Ala Leu Pro
1385              1390              1395

Ile Glu Tyr Gly Pro Leu Val Glu Glu Glu Glu Lys Val Pro Val
1400              1405              1410

Arg Pro Lys Asp Pro Glu Gly Val Pro Pro Leu Leu Val Ser Gln
1415              1420              1425

Gln Ala Lys Arg Glu Glu Glu Arg Ser Pro Ala Ala Pro Pro Pro
1430              1435              1440

Leu Pro Thr Thr Ser Ser Gly Lys Ala Ala Lys Lys Pro Thr Ala
1445              1450              1455

Ala Glu Val Ser Val Arg Val Pro Arg Gly Pro Ala Val Glu Gly
1460              1465              1470

Gly His Val Asn Met Ala Phe Ser Gln Ser Asn Pro Pro Ser Glu
1475              1480              1485

Leu His Lys Val His Gly Ser Arg Asn Lys Pro Thr Ser Leu Trp
1490              1495              1500

Asn Pro Thr Tyr Gly Ser Trp Phe Thr Glu Lys Pro Thr Lys Lys
1505              1510              1515

Asn Asn Pro Ile Ala Lys Lys Glu Pro His Asp Arg Gly Asn Leu
1520              1525              1530

Gly Leu Glu Gly Ser Cys Thr Val Pro Pro Asn Val Ala Thr Gly
1535              1540              1545

```
Arg Leu Pro Gly Ala Ser Leu Leu Glu Pro Ser Ser Leu Thr
    1550                1555                1560

Ala Asn Met Lys Glu Val Pro Leu Phe Arg Leu Arg His Phe Pro
    1565                1570                1575

Cys Gly Asn Val Asn Tyr Tyr Gln Gln Gln Gly Leu Pro Leu
    1580                1585                1590

Glu Ala Ala Thr Ala Pro Gly Ala Gly His Tyr Glu Asp Thr Ile
    1595                1600                1605

Leu Lys Ser Lys Asn Ser Met Asn Gln Pro Gly Pro
    1610                1615                1620

<210> SEQ ID NO 3
<211> LENGTH: 277
<212> TYPE: PRT
<213> ORGANISM: Artificial Sequence
<220> FEATURE:
<223> OTHER INFORMATION: Synthetic Peptide

<400> SEQUENCE: 3

Ile Thr Leu Ile Arg Gly Leu Gly His Gly Ala Phe Gly Glu Val Tyr
1               5                   10                  15

Glu Gly Gln Val Ser Gly Met Pro Asn Asp Pro Ser Pro Leu Gln Val
            20                  25                  30

Ala Val Lys Thr Leu Pro Glu Val Cys Ser Glu Gln Asp Glu Leu Asp
        35                  40                  45

Phe Leu Met Glu Ala Leu Ile Ile Ser Lys Phe Asn His Gln Asn Ile
    50                  55                  60

Val Arg Cys Ile Gly Val Ser Leu Gln Ser Leu Pro Arg Phe Ile Leu
65                  70                  75                  80

Leu Glu Leu Met Ala Gly Gly Asp Leu Lys Ser Phe Leu Arg Glu Thr
                85                  90                  95

Arg Pro Arg Pro Ser Gln Pro Ser Ser Leu Ala Met Leu Asp Leu Leu
            100                 105                 110

His Val Ala Arg Asp Ile Ala Cys Gly Cys Gln Tyr Leu Glu Glu Asn
        115                 120                 125

His Phe Ile His Arg Asp Ile Ala Ala Arg Asn Cys Leu Leu Thr Cys
    130                 135                 140

Pro Gly Pro Gly Arg Val Ala Lys Ile Gly Asp Phe Gly Met Ala Arg
145                 150                 155                 160

Asp Ile Tyr Arg Ala Ser Tyr Tyr Arg Lys Gly Gly Cys Ala Met Leu
                165                 170                 175

Pro Val Lys Trp Met Pro Pro Glu Ala Phe Met Glu Gly Ile Phe Thr
            180                 185                 190

Ser Lys Thr Asp Thr Trp Ser Phe Gly Val Leu Leu Trp Glu Ile Phe
        195                 200                 205

Ser Leu Gly Tyr Met Pro Tyr Pro Ser Lys Ser Asn Gln Glu Val Leu
    210                 215                 220

Glu Phe Val Thr Ser Gly Gly Arg Met Asp Pro Pro Lys Asn Cys Pro
225                 230                 235                 240

Gly Pro Val Tyr Arg Ile Met Thr Gln Cys Trp Gln His Gln Pro Glu
                245                 250                 255

Asp Arg Pro Asn Phe Ala Ile Ile Leu Glu Arg Ile Glu Tyr Cys Thr
            260                 265                 270

Gln Asp Pro Asp Val
        275
```

```
<210> SEQ ID NO 4
<211> LENGTH: 561
<212> TYPE: PRT
<213> ORGANISM: Artificial Sequence
<220> FEATURE:
<223> OTHER INFORMATION: Synthetic Peptide

<400> SEQUENCE: 4

Arg Arg Lys His Gln Glu Leu Gln Ala Met Gln Met Glu Leu Gln Ser
1               5                   10                  15

Pro Glu Tyr Lys Leu Ser Lys Leu Arg Thr Ser Thr Ile Met Thr Asp
            20                  25                  30

Tyr Asn Pro Asn Tyr Cys Phe Ala Gly Lys Thr Ser Ser Ile Ser Asp
        35                  40                  45

Leu Lys Glu Val Pro Arg Lys Asn Ile Thr Leu Ile Arg Gly Leu Gly
    50                  55                  60

His Gly Ala Phe Gly Glu Val Tyr Glu Gly Gln Val Ser Gly Met Pro
65                  70                  75                  80

Asn Asp Pro Ser Pro Leu Gln Val Ala Val Lys Thr Leu Pro Glu Val
                85                  90                  95

Cys Ser Glu Gln Asp Glu Leu Asp Phe Leu Met Glu Ala Leu Ile Ile
            100                 105                 110

Ser Lys Phe Asn His Gln Asn Ile Val Arg Cys Ile Gly Val Ser Leu
        115                 120                 125

Gln Ser Leu Pro Arg Phe Ile Leu Leu Glu Leu Met Ala Gly Gly Asp
    130                 135                 140

Leu Lys Ser Phe Leu Arg Glu Thr Arg Pro Arg Pro Ser Gln Pro Ser
145                 150                 155                 160

Ser Leu Ala Met Leu Asp Leu Leu His Val Ala Arg Asp Ile Ala Cys
                165                 170                 175

Gly Cys Gln Tyr Leu Glu Glu Asn His Phe Ile His Arg Asp Ile Ala
            180                 185                 190

Ala Arg Asn Cys Leu Leu Thr Cys Pro Gly Pro Gly Arg Val Ala Lys
        195                 200                 205

Ile Gly Asp Phe Gly Met Ala Arg Asp Ile Tyr Arg Ala Ser Tyr Tyr
    210                 215                 220

Arg Lys Gly Gly Cys Ala Met Leu Pro Val Lys Trp Met Pro Pro Glu
225                 230                 235                 240

Ala Phe Met Glu Gly Ile Phe Thr Ser Lys Thr Asp Thr Trp Ser Phe
                245                 250                 255

Gly Val Leu Leu Trp Glu Ile Phe Ser Leu Gly Tyr Met Pro Tyr Pro
            260                 265                 270

Ser Lys Ser Asn Gln Glu Val Leu Glu Phe Val Thr Ser Gly Gly Arg
        275                 280                 285

Met Asp Pro Pro Lys Asn Cys Pro Gly Pro Val Tyr Arg Ile Met Thr
    290                 295                 300

Gln Cys Trp Gln His Gln Pro Glu Asp Arg Pro Asn Phe Ala Ile Ile
305                 310                 315                 320

Leu Glu Arg Ile Glu Tyr Cys Thr Gln Asp Pro Asp Val Ile Asn Thr
                325                 330                 335

Ala Leu Pro Ile Glu Tyr Gly Pro Leu Val Glu Glu Glu Lys Val
            340                 345                 350

Pro Val Arg Pro Lys Asp Pro Glu Gly Val Pro Pro Leu Leu Val Ser
        355                 360                 365
```

Gln Gln Ala Lys Arg Glu Glu Arg Ser Pro Ala Pro Pro
370                 375                 380

Leu Pro Thr Thr Ser Ser Gly Lys Ala Ala Lys Lys Pro Thr Ala Ala
385                 390                 395                 400

Glu Ile Ser Val Arg Val Pro Arg Gly Pro Ala Val Glu Gly His
                405                 410                 415

Val Asn Met Ala Phe Ser Gln Ser Asn Pro Ser Glu Leu His Lys
            420                 425                 430

Val His Gly Ser Arg Asn Lys Pro Thr Ser Leu Trp Asn Pro Thr Tyr
        435                 440                 445

Gly Ser Trp Phe Thr Glu Lys Pro Thr Lys Asn Asn Pro Ile Ala
450                 455                 460

Lys Lys Glu Pro His Asp Arg Gly Asn Leu Gly Leu Glu Gly Ser Cys
465                 470                 475                 480

Thr Val Pro Pro Asn Val Ala Thr Gly Arg Leu Pro Gly Ala Ser Leu
                485                 490                 495

Leu Leu Glu Pro Ser Ser Leu Thr Ala Asn Met Lys Glu Val Pro Leu
                500                 505                 510

Phe Arg Leu Arg His Phe Pro Cys Gly Asn Val Asn Tyr Gly Tyr Gln
515                 520                 525

Gln Gln Gly Leu Pro Leu Glu Ala Ala Thr Ala Pro Gly Ala Gly His
        530                 535                 540

Tyr Glu Asp Thr Ile Leu Lys Ser Lys Asn Ser Met Asn Gln Pro Gly
545                 550                 555                 560

Pro

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Asn Pro Thr Tyr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

His Tyr Glu Asp
1

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7
aggagagaaa gagctgcagt g                                            21

<210> SEQ ID NO 8
<211> LENGTH: 24

<212> TYPE: DNA
<213> ORGANISM: Artificial Sequence
<220> FEATURE:
<223> OTHER INFORMATION: Synthetic Polynucleotide

<400> SEQUENCE: 8
gctctgaacc tttccatcat actt								24

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
actggtcccc agacaacaag									20

<210> SEQ ID NO 10
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 10
ttactctgtc aaattgatgc tgct								24

<210> SEQ ID NO 11
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 11
catgaggaaa tccagttcgt cctg								24

<210> SEQ ID NO 12
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 12
gaggtcttgc cagcaaagca gtag								24

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
aacgaccact ttgtcaagct c									21

<210> SEQ ID NO 14
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 14
ctctcttcct cttgtgctct tgc                                           23

<210> SEQ ID NO 15
<211> LENGTH: 562
<212> TYPE: PRT
<213> ORGANISM: Artificial Sequence
<220> FEATURE:
<223> OTHER INFORMATION: Synthetic Peptide

<400> SEQUENCE: 15

```
Tyr Arg Arg Lys His Gln Glu Leu Gln Ala Met Gln Met Glu Leu Gln
1               5                   10                  15

Ser Pro Glu Tyr Lys Leu Ser Lys Leu Arg Thr Ser Thr Ile Met Thr
            20                  25                  30

Asp Tyr Asn Pro Asn Tyr Cys Phe Ala Gly Lys Thr Ser Ser Ile Ser
        35                  40                  45

Asp Leu Lys Glu Val Pro Arg Lys Asn Ile Thr Leu Ile Arg Gly Leu
    50                  55                  60

Gly His Gly Ala Phe Gly Glu Val Tyr Glu Gly Gln Val Ser Gly Met
65                  70                  75                  80

Pro Asn Asp Pro Ser Pro Leu Gln Val Ala Val Lys Thr Leu Pro Glu
                85                  90                  95

Val Cys Ser Glu Gln Asp Glu Leu Asp Phe Leu Met Glu Ala Leu Ile
            100                 105                 110

Ile Ser Lys Phe Asn His Gln Asn Ile Val Arg Cys Ile Gly Val Ser
        115                 120                 125

Leu Gln Ser Leu Pro Arg Phe Ile Leu Leu Glu Leu Met Ala Gly Gly
    130                 135                 140

Asp Leu Lys Ser Phe Leu Arg Glu Thr Arg Pro Arg Pro Ser Gln Pro
145                 150                 155                 160

Ser Ser Leu Ala Met Leu Asp Leu Leu His Val Ala Arg Asp Ile Ala
                165                 170                 175

Cys Gly Cys Gln Tyr Leu Glu Glu Asn His Phe Ile His Arg Asp Ile
            180                 185                 190

Ala Ala Arg Asn Cys Leu Leu Thr Cys Pro Gly Pro Gly Arg Val Ala
        195                 200                 205

Lys Ile Gly Asp Phe Gly Met Ala Arg Asp Ile Tyr Arg Ala Ser Tyr
    210                 215                 220

Tyr Arg Lys Gly Gly Cys Ala Met Leu Pro Val Lys Trp Met Pro Pro
225                 230                 235                 240

Glu Ala Phe Met Glu Gly Ile Phe Thr Ser Lys Thr Asp Thr Trp Ser
                245                 250                 255

Phe Gly Val Leu Leu Trp Glu Ile Phe Ser Leu Gly Tyr Met Pro Tyr
            260                 265                 270

Pro Ser Lys Ser Asn Gln Glu Val Leu Glu Phe Val Thr Ser Gly Gly
        275                 280                 285

Arg Met Asp Pro Pro Lys Asn Cys Pro Gly Pro Val Tyr Arg Ile Met
    290                 295                 300

Thr Gln Cys Trp Gln His Gln Pro Glu Asp Arg Pro Asn Phe Ala Ile
305                 310                 315                 320

Ile Leu Glu Arg Ile Glu Tyr Cys Thr Gln Asp Pro Asp Val Ile Asn
                325                 330                 335

Thr Ala Leu Pro Ile Glu Tyr Gly Pro Leu Val Glu Glu Glu Glu Lys
            340                 345                 350

Val Pro Val Arg Pro Lys Asp Pro Glu Gly Val Pro Pro Leu Leu Val
```

```
                    355                 360                 365
Ser Gln Gln Ala Lys Arg Glu Glu Arg Ser Pro Ala Ala Pro Pro
    370                 375                 380

Pro Leu Pro Thr Thr Ser Ser Gly Lys Ala Ala Lys Lys Pro Thr Ala
385                 390                 395                 400

Ala Glu Val Ser Val Arg Val Pro Arg Gly Pro Ala Val Glu Gly Gly
            405                 410                 415

His Val Asn Met Ala Phe Ser Gln Ser Asn Pro Pro Ser Glu Leu His
        420                 425                 430

Lys Val His Gly Ser Arg Asn Lys Pro Thr Ser Leu Trp Asn Pro Thr
        435                 440                 445

Tyr Gly Ser Trp Phe Thr Glu Lys Pro Thr Lys Lys Asn Asn Pro Ile
    450                 455                 460

Ala Lys Lys Glu Pro His Asp Arg Gly Asn Leu Gly Leu Glu Gly Ser
465                 470                 475                 480

Cys Thr Val Pro Pro Asn Val Ala Thr Gly Arg Leu Pro Gly Ala Ser
                485                 490                 495

Leu Leu Leu Glu Pro Ser Ser Leu Thr Ala Asn Met Lys Glu Val Pro
            500                 505                 510

Leu Phe Arg Leu Arg His Phe Pro Cys Gly Asn Val Asn Tyr Gly Tyr
        515                 520                 525

Gln Gln Gln Gly Leu Pro Leu Glu Ala Ala Thr Ala Pro Gly Ala Gly
        530                 535                 540

His Tyr Glu Asp Thr Ile Leu Lys Ser Lys Asn Ser Met Asn Gln Pro
545                 550                 555                 560

Gly Pro
```